US010799251B2

(12) United States Patent
Altschuler et al.

(10) Patent No.: US 10,799,251 B2
(45) Date of Patent: Oct. 13, 2020

(54) TOOLS AND SYSTEMS FOR SOLID FORM AND GRAFT IMPLANTATION

(71) Applicant: Cartiheal (2009) Ltd., Kfar Saba (IL)

(72) Inventors: Nir Altschuler, Tzur Yitzchak (IL); Amir Goren, Yahud (IL)

(73) Assignee: Cartiheal (2009) Ltd., Kfar Saba (IL)

( * ) Notice: Subject to any disclaimer, the term of this patent is extended or adjusted under 35 U.S.C. 154(b) by 91 days.

(21) Appl. No.: 15/998,981

(22) Filed: Aug. 20, 2018

(65) Prior Publication Data

US 2019/0053815 A1    Feb. 21, 2019

Related U.S. Application Data

(63) Continuation of application No. 14/441,985, filed as application No. PCT/IL2013/050925 on Nov. 11, 2013, now abandoned.

(60) Provisional application No. 61/725,046, filed on Nov. 12, 2012.

(51) Int. Cl.
*A61B 17/17* (2006.01)
*A61B 17/88* (2006.01)

(52) U.S. Cl.
CPC .......... *A61B 17/17* (2013.01); *A61B 17/8894* (2013.01)

(58) Field of Classification Search
CPC .. A61B 17/1635; A61B 17/17; A61B 17/8894
USPC .......................................................... 606/96
See application file for complete search history.

(56) References Cited

U.S. PATENT DOCUMENTS

| 5,489,307 | A | * | 2/1996 | Kuslich | A61F 2/4611 |
| | | | | | 128/898 |
| 5,718,707 | A | * | 2/1998 | Mikhail | A61F 2/4601 |
| | | | | | 606/94 |
| 5,860,946 | A | * | 1/1999 | Hofstatter | A61M 31/007 |
| | | | | | 604/15 |
| 6,017,348 | A | * | 1/2000 | Hart | A61B 17/1637 |
| | | | | | 606/179 |
| 6,063,088 | A | * | 5/2000 | Winslow | A61B 17/1757 |
| | | | | | 606/86 A |
| 6,110,178 | A | * | 8/2000 | Zech | A61B 17/1635 |
| | | | | | 606/96 |
| 6,270,502 | B1 | | 8/2001 | Stulberg | |
| 6,306,142 | B1 | * | 10/2001 | Johanson | A61B 10/025 |
| | | | | | 606/79 |
| 6,358,253 | B1 | * | 3/2002 | Torrie | A61F 2/4657 |
| | | | | | 606/96 |
| 6,530,928 | B1 | * | 3/2003 | Frei | A61B 17/1637 |
| | | | | | 606/80 |

(Continued)

OTHER PUBLICATIONS

International Search Report (ISR) for PCT/IL2013/050925; I.A. fd Nov. 11, 2013, dated May 9, 2014 from the European Patent Office, Rijswijk, Netherlands.

(Continued)

*Primary Examiner* — Eric S Gibson
(74) *Attorney, Agent, or Firm* — Sterne, Kessler, Goldstein & Fox P.L.L.C.

(57) ABSTRACT

This invention provides tools and kits for removal of a graft and/or for implantation of a solid or semi-solid form or graft within an appropriate desired tissue minimizing the potential for or actual breakage of the implant or graft during the stated process. Kits comprising such tools and methods making use of same are provided, as well.

19 Claims, 18 Drawing Sheets

(56) References Cited

U.S. PATENT DOCUMENTS

| | | | | |
|---|---|---|---|---|
| 6,582,438 B2* | 6/2003 | DeMayo | ............ | A61B 17/7095 606/92 |
| 7,141,074 B2* | 11/2006 | Fanger | ............... | A61B 17/1617 606/80 |
| 7,572,291 B2* | 8/2009 | Gil | ...................... | A61F 2/30756 623/14.12 |
| 7,758,583 B2* | 7/2010 | Gil | ........................ | A61F 2/4618 606/110 |
| 8,435,305 B2* | 5/2013 | Lozier | .................. | A61F 2/4601 606/86 R |
| 8,753,406 B2* | 6/2014 | Lozier | .................. | A61F 2/4601 606/99 |
| 8,821,494 B2* | 9/2014 | Pilgeram | ............ | A61B 17/0401 606/80 |
| 8,911,445 B2* | 12/2014 | Rocci | ................. | A61B 17/1686 606/86 R |
| 2005/0038444 A1* | 2/2005 | Binder, Jr. | ......... | A61B 17/1728 606/96 |
| 2005/0137600 A1* | 6/2005 | Jacobs | ............... | A61B 17/1615 606/79 |
| 2005/0234467 A1* | 10/2005 | Rains | ................ | A61B 17/1728 606/96 |
| 2006/0247652 A1* | 11/2006 | Heinz | ................ | A61B 17/8819 606/92 |
| 2007/0043376 A1* | 2/2007 | Leatherbury | ...... | A61B 17/1635 606/99 |
| 2007/0149982 A1* | 6/2007 | Lyons | ................ | A61B 17/1604 606/99 |
| 2007/0191852 A1* | 8/2007 | Shimko | .............. | A61B 17/1604 606/79 |
| 2007/0270711 A1* | 11/2007 | Gil | ........................ | A61B 10/025 600/567 |
| 2008/0195115 A1* | 8/2008 | Oren | .................... | A61F 2/4601 606/96 |
| 2008/0221581 A1* | 9/2008 | Shoham | ................ | A61B 17/17 606/96 |
| 2008/0262616 A1* | 10/2008 | McKay | .............. | A61B 17/1635 623/14.12 |
| 2008/0306608 A1* | 12/2008 | Nycz | ..................... | A61B 6/481 623/23.57 |
| 2009/0024224 A1* | 1/2009 | Chen | .................. | A61B 17/1604 623/23.72 |
| 2009/0054906 A1* | 2/2009 | Walthall | ............. | A61B 17/1635 606/108 |
| 2009/0187194 A1* | 7/2009 | Hamada | ............. | A61B 17/7001 606/104 |
| 2009/0299371 A1* | 12/2009 | Steiner | ............... | A61B 17/1675 606/79 |
| 2009/0319051 A9 | 12/2009 | Nycz et al. | | |
| 2010/0292704 A1* | 11/2010 | Stoffel | .................. | A61F 2/4601 606/99 |
| 2011/0009872 A1* | 1/2011 | Mistry | .................. | A61F 2/4603 606/99 |
| 2011/0125272 A1* | 5/2011 | Bagga | .................... | A61B 17/68 623/18.11 |
| 2011/0256228 A1* | 10/2011 | Altschuler | ............. | A61K 45/06 424/491 |
| 2012/0053642 A1* | 3/2012 | Lozier | .................... | A61F 2/4601 606/86 R |
| 2012/0109143 A1* | 5/2012 | Steele | ................ | A61B 17/7082 606/104 |
| 2012/0197261 A1* | 8/2012 | Rocci | ................. | A61B 17/1686 606/96 |
| 2013/0023881 A1* | 1/2013 | Cook | ..................... | A61B 17/17 606/80 |
| 2013/0304068 A1* | 11/2013 | Larche | ................. | A61B 17/888 606/79 |
| 2015/0142067 A1* | 5/2015 | Bess | ................... | A61B 17/8894 606/86 A |
| 2015/0157469 A1* | 6/2015 | Prado | .................... | A61F 2/4601 606/86 A |
| 2015/0250485 A1* | 9/2015 | Niederberger | ..... | A61B 17/1728 606/281 |
| 2015/0289889 A1* | 10/2015 | Altschuler | ............. | A61B 17/88 606/87 |
| 2016/0250042 A1* | 9/2016 | Wahl | .................... | A61F 2/4618 623/18.11 |
| 2016/0331429 A1* | 11/2016 | Jensen | .................. | A61F 2/4601 |

OTHER PUBLICATIONS

International Preliminary Report on Patentability (Chapter II of the Patent Cooperation Treaty) for PCT/IL2013/050925; I.A. fd Nov. 11, 2013, completed Jan. 27, 2015, from the European Patent Office, Munich, Germany.

* cited by examiner

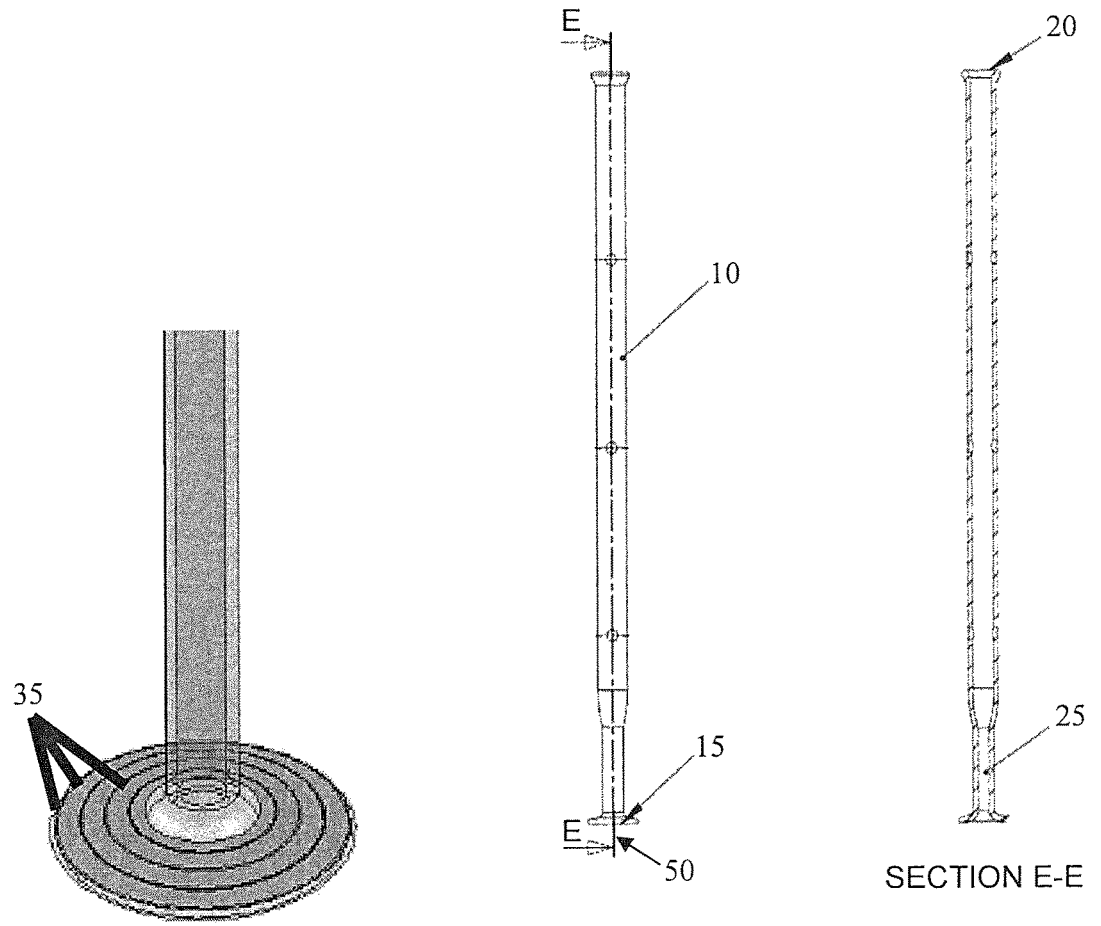
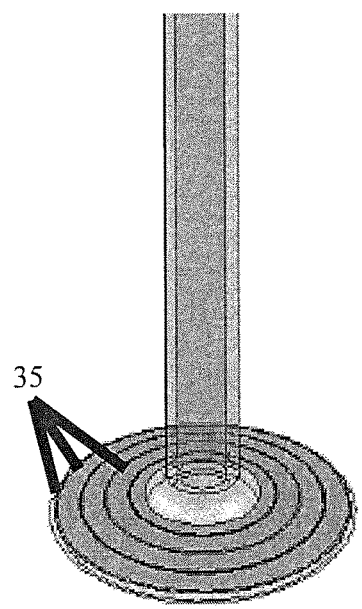
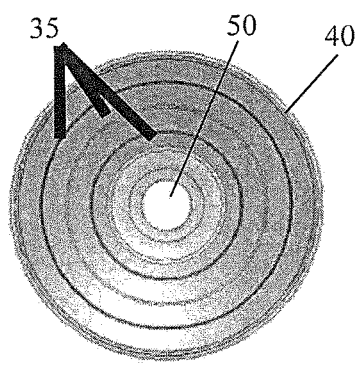
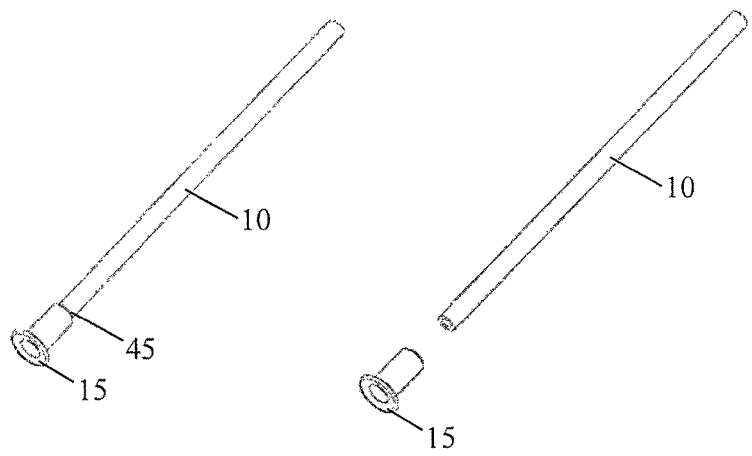
Figure 1A　　Figure 1B　　Figure 1C
Figure 1D　　Figure 1E　　Figure 1F

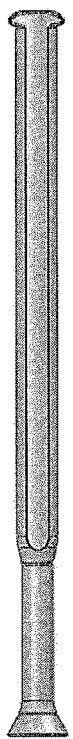
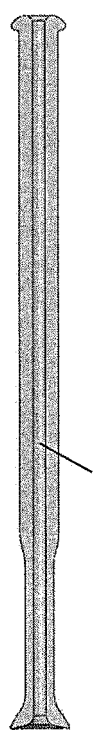
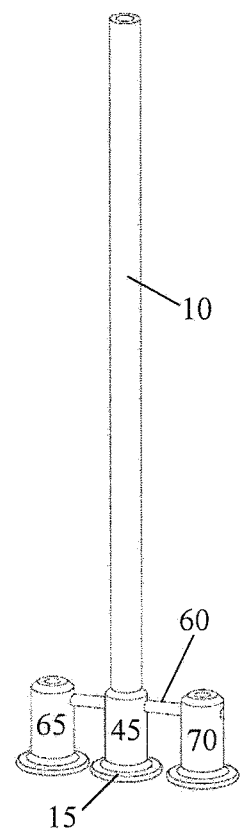
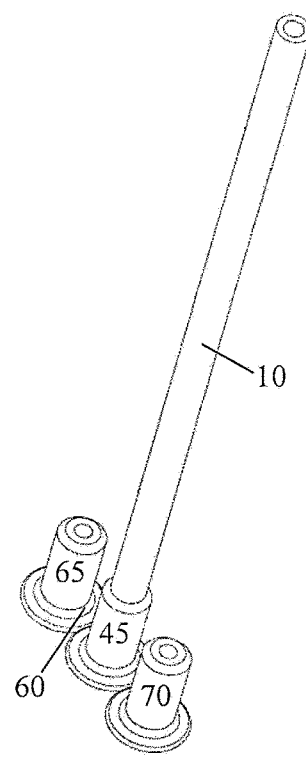
Figure 1G   Figure 1H   Figure 2A   Figure 2B
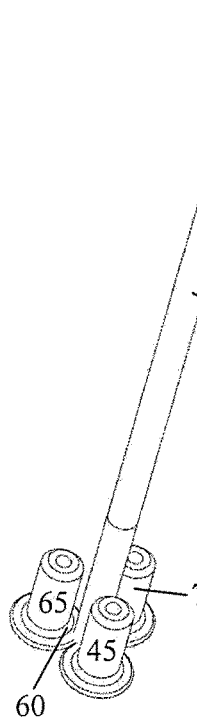
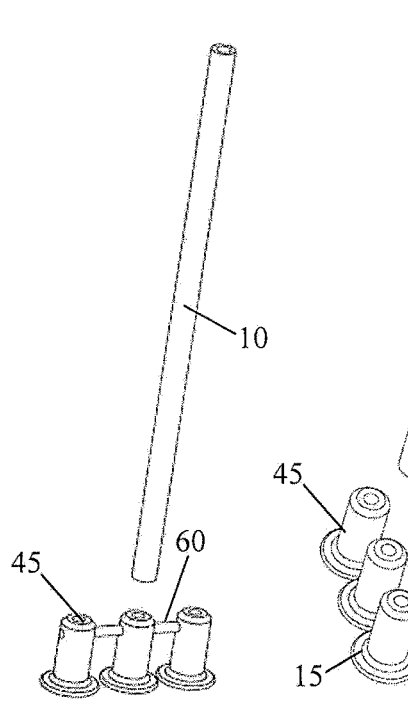
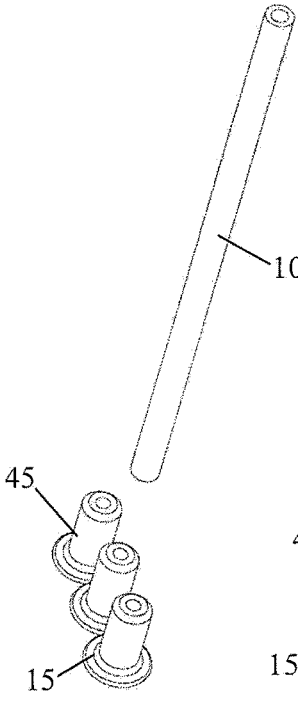
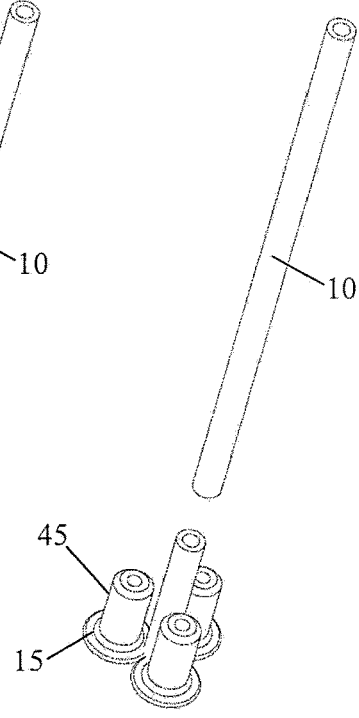
Figure 2C   Figure 2D   Figure 2E   Figure 2F

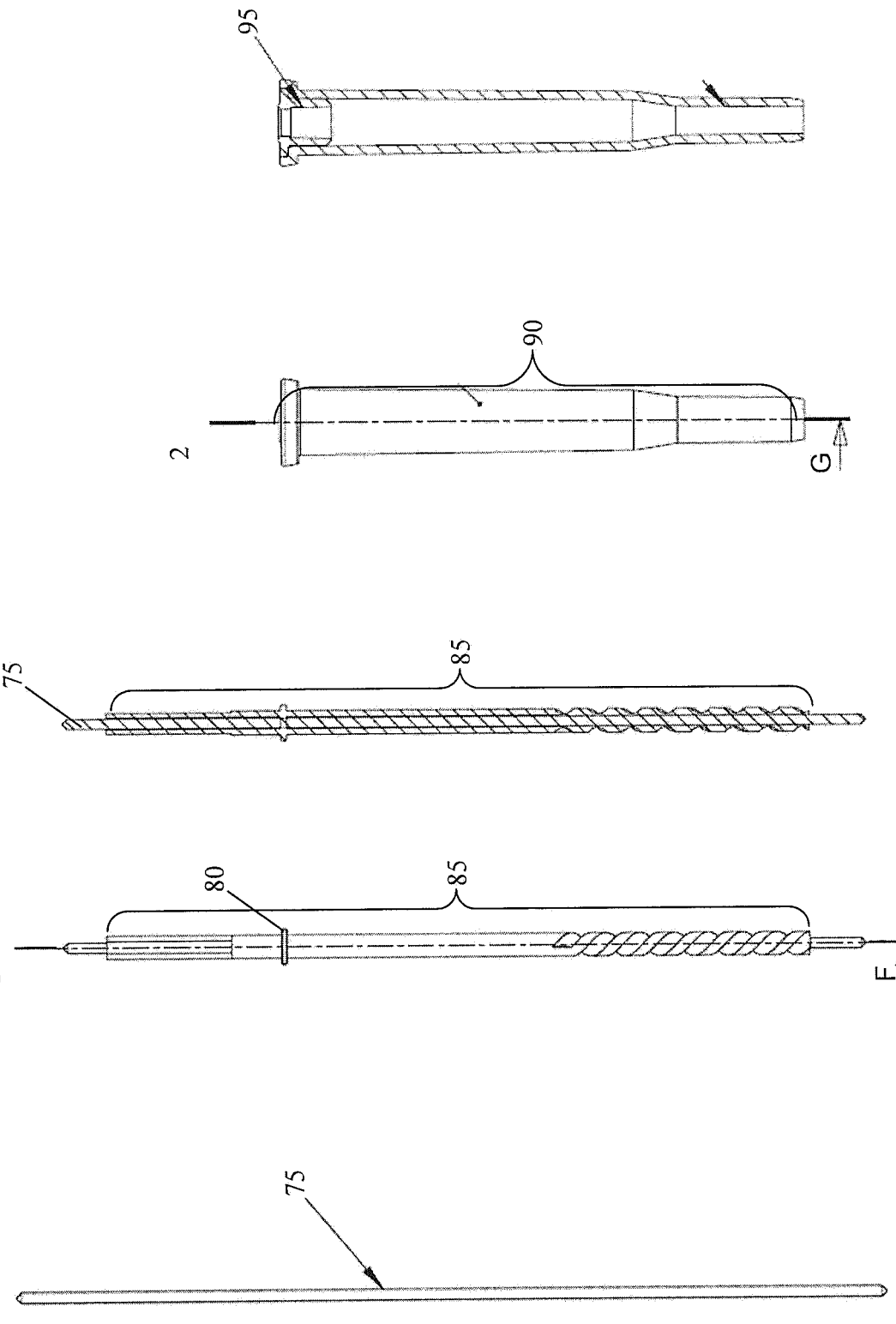

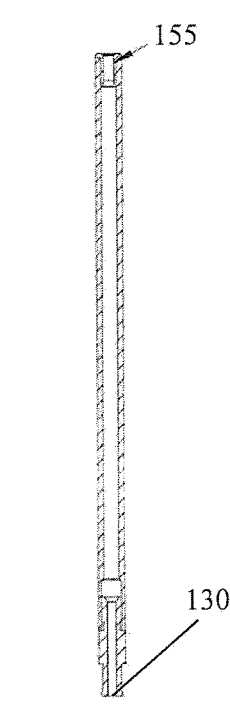
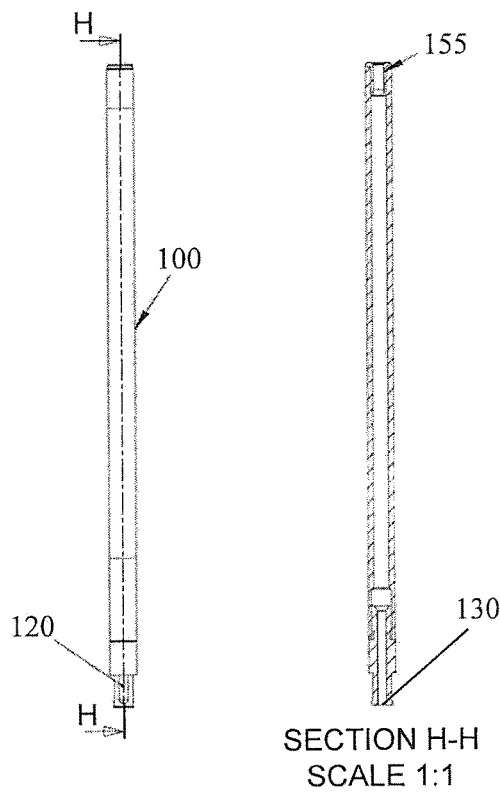
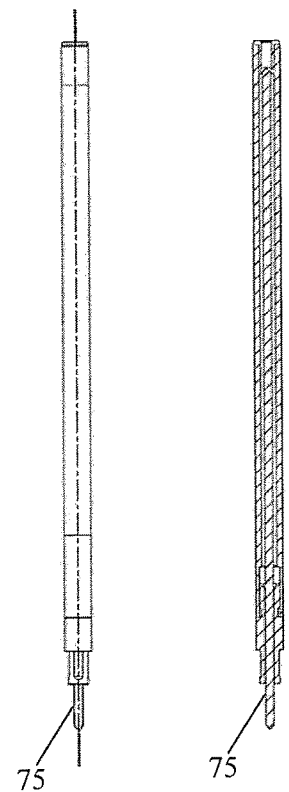
Figure 4A    Figure 4B    Figure 4C  Figure 4D
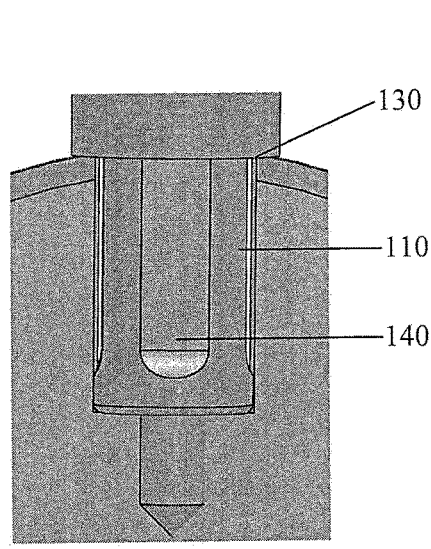 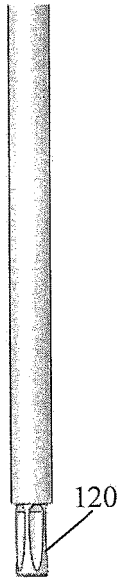 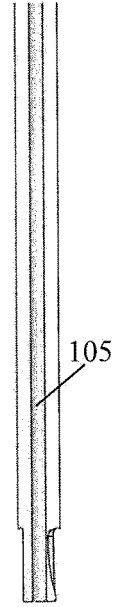 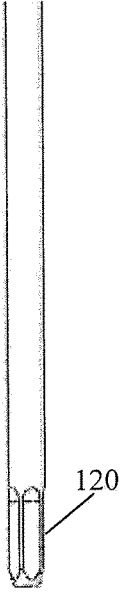 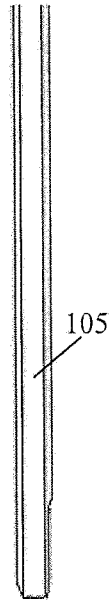
Figure 4E    Figure 4F  Figure 4G  Figure 4H  Figure 4I

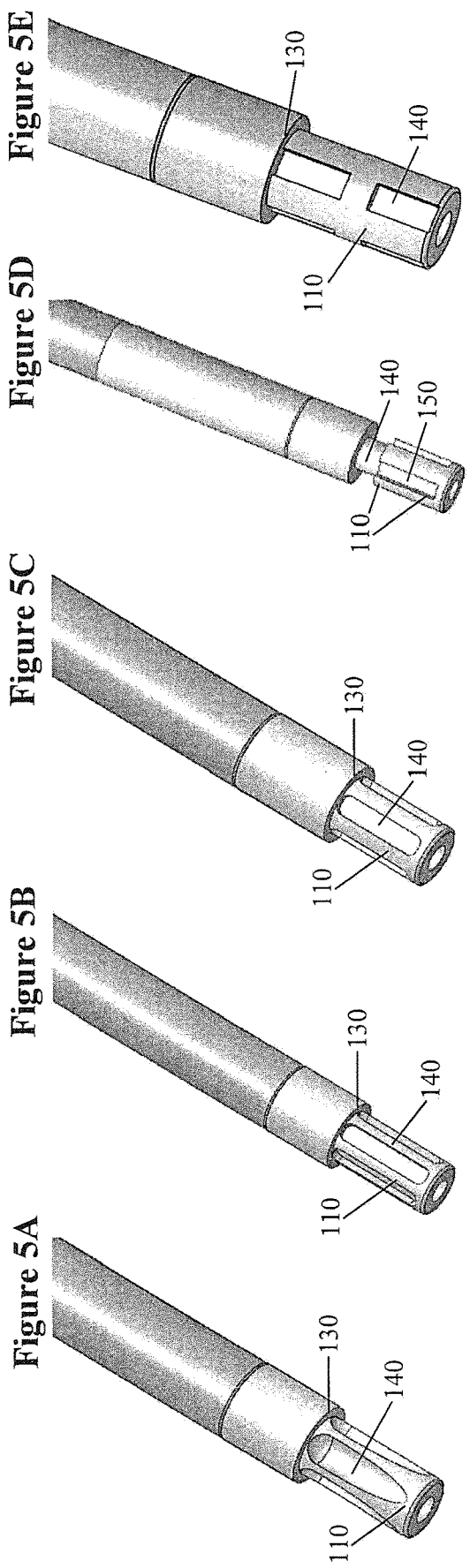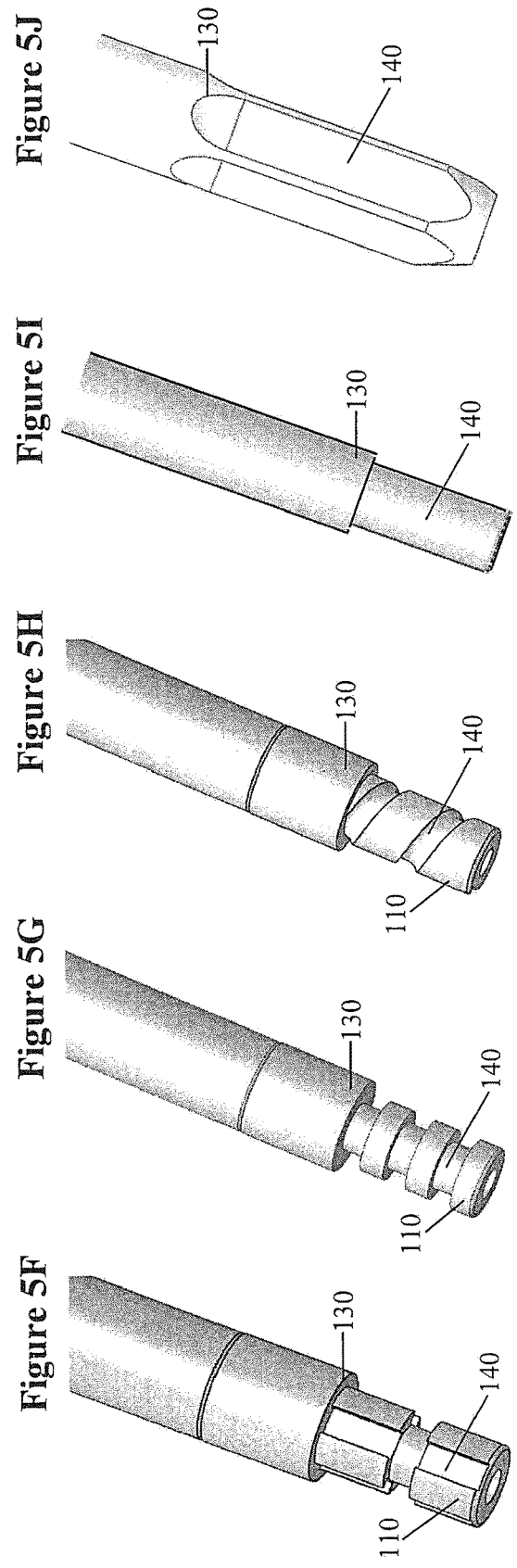

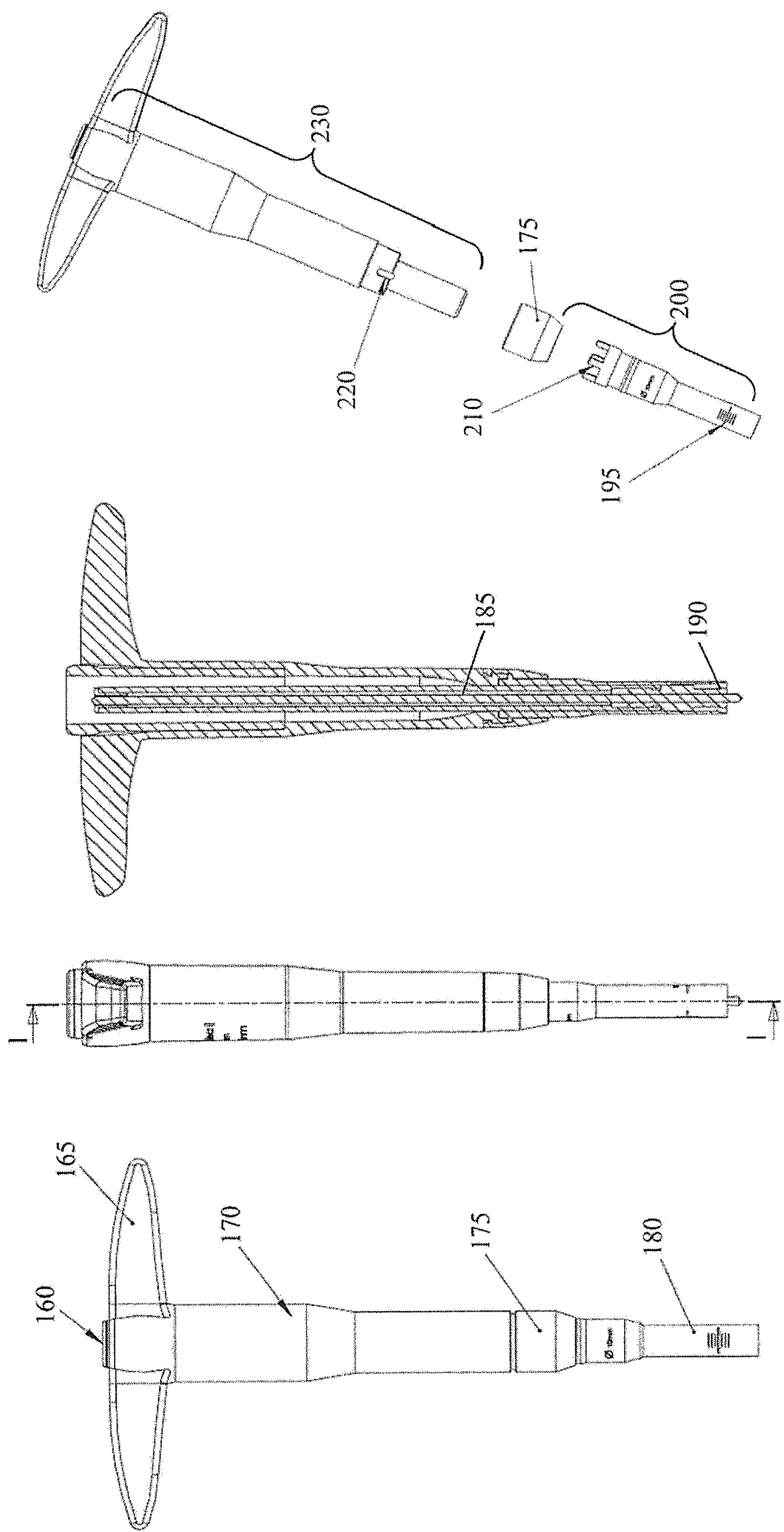

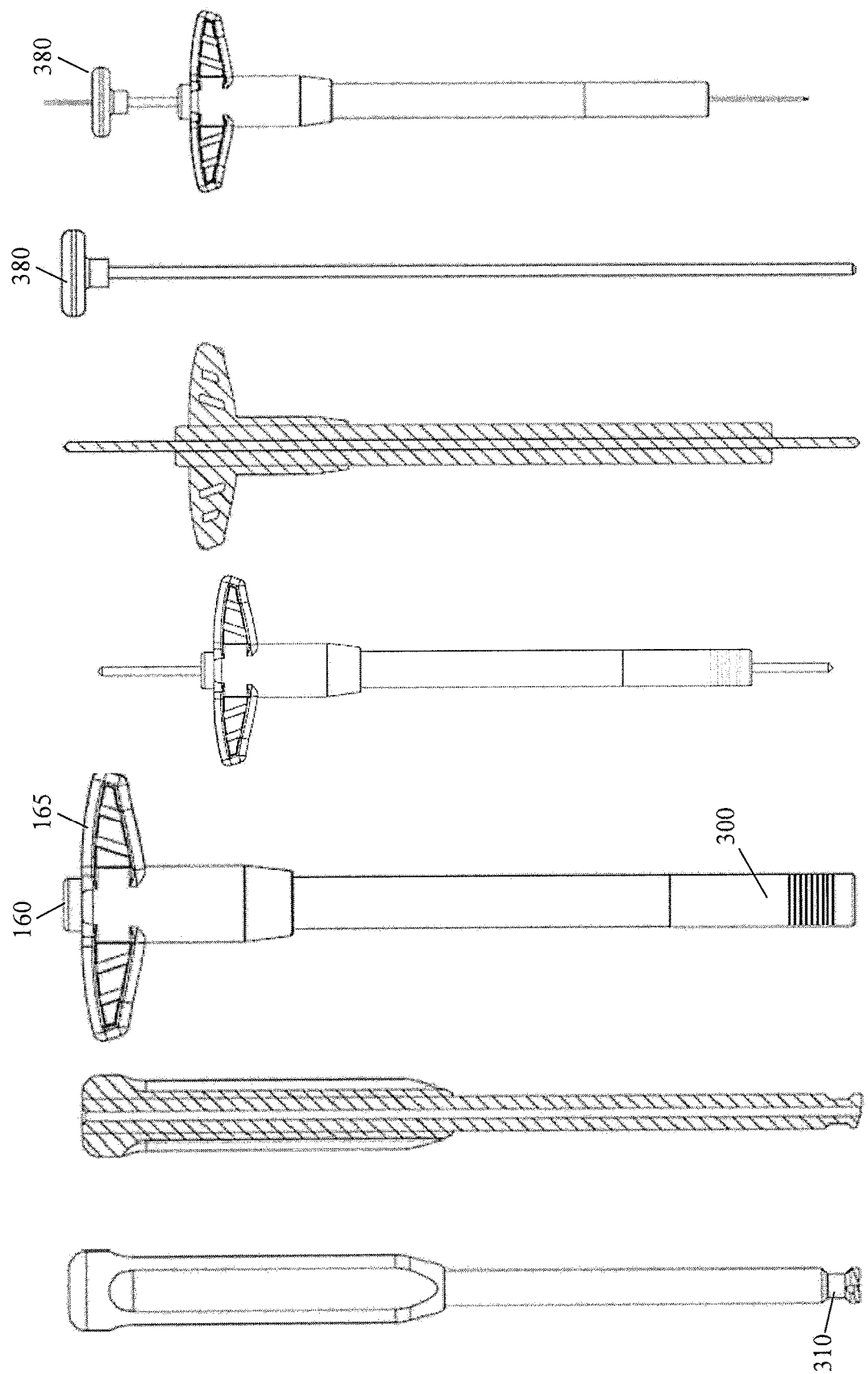

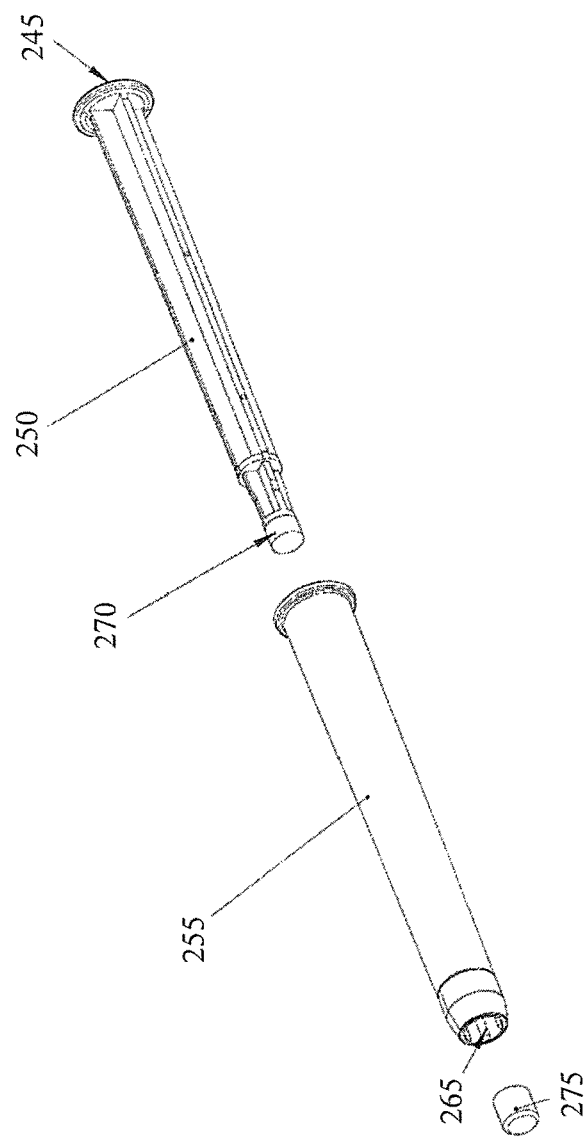
Figure 9C
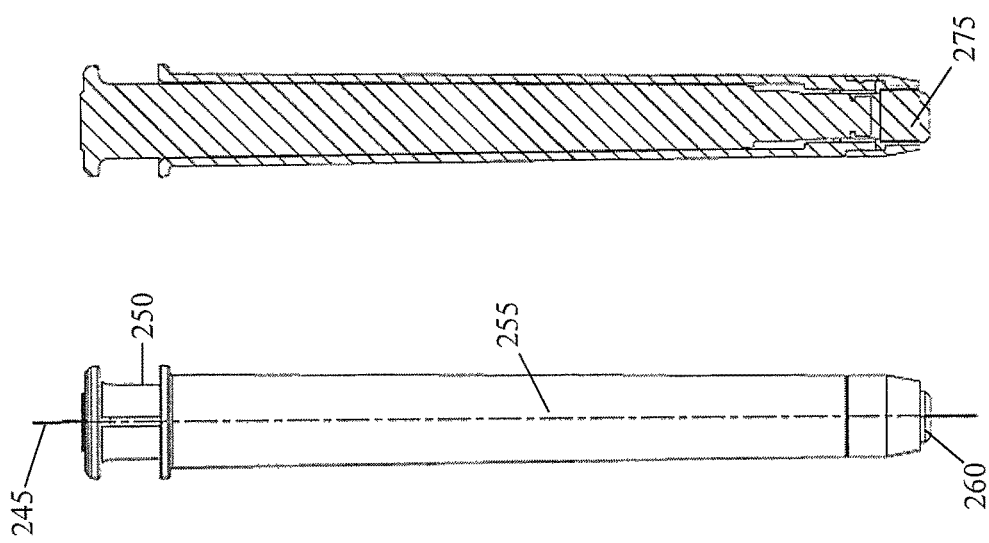
Figure 9B
Figure 9A

SECTION D-D
SCALE 1:1

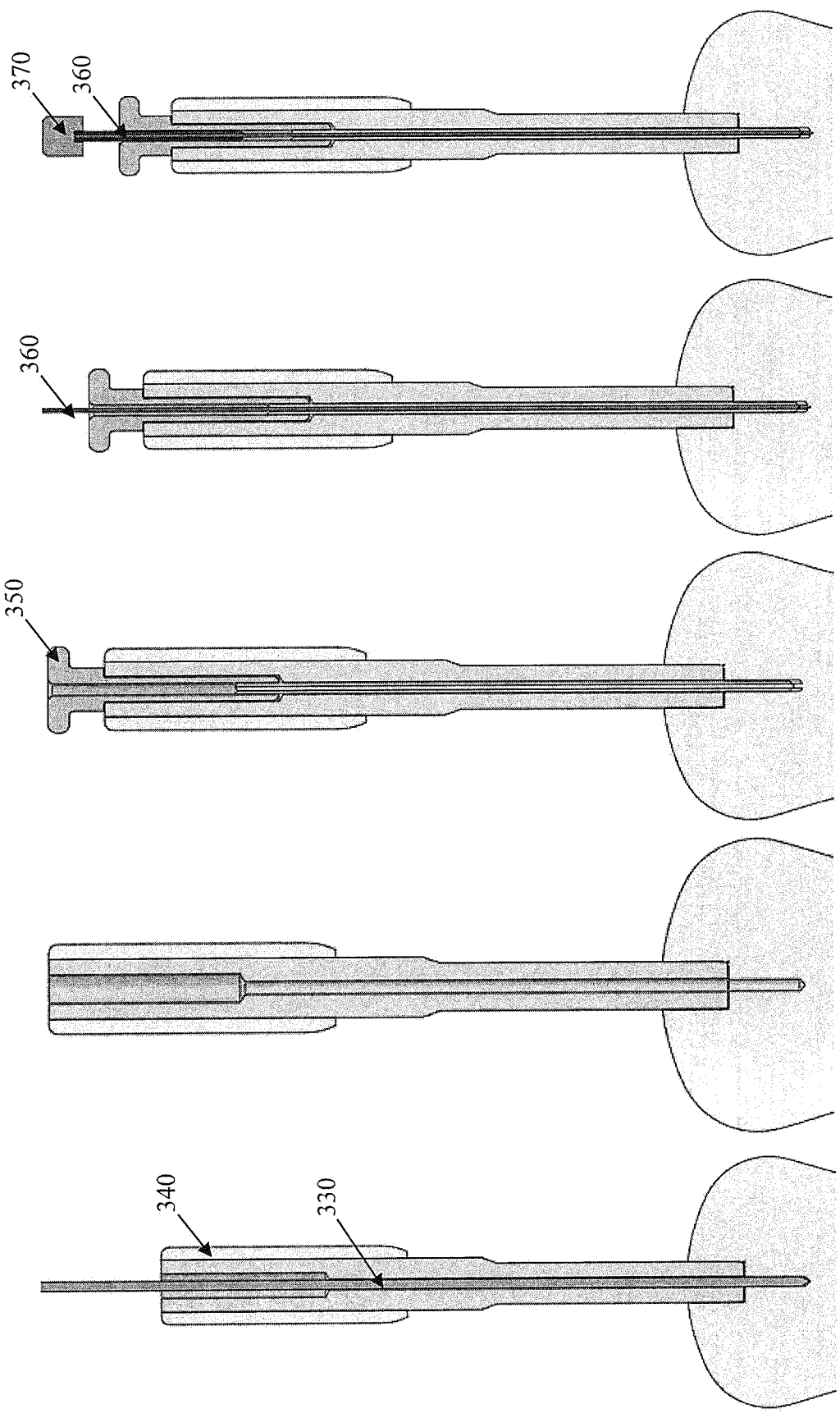

```
┌─────────────────────────────────────────────────────────────────────────────┐
│ The implantation tool stabilizing implement is placed on an articular surface. The │
│ stabilizing implement is positioned and stabilized with the help of the stabilizing │
│ contact structure onto the desired implantation location.                   │
└─────────────────────────────────────────────────────────────────────────────┘
                                      ↓
┌─────────────────────────────────────────────────────────────────────────────┐
│ A rod-like structure such as a K-wire is thread through the stabilizing Implement │
│ and anchored perpendicularly to the articular surface and within bone (20-40mm). │
└─────────────────────────────────────────────────────────────────────────────┘
                                      ↓
┌─────────────────────────────────────────────────────────────────────────────┐
│ The stabilizing implement is removed. A cannulated drill bit is positioned over the │
│ K-wire. A drill drill bit protective sheath may be used, as well.           │
└─────────────────────────────────────────────────────────────────────────────┘
                                      ↓
┌─────────────────────────────────────────────────────────────────────────────┐
│ The cannulated drill prepares a first introductory hole in the tissue, the depth of │
│ which is controlled, e.g. by a stopper on the stabilizing implement.        │
└─────────────────────────────────────────────────────────────────────────────┘
                                      ↓
┌─────────────────────────────────────────────────────────────────────────────┐
│ The cannulated drill bit and the drill sleeve will be removed.              │
└─────────────────────────────────────────────────────────────────────────────┘
                                      ↓
┌─────────────────────────────────────────────────────────────────────────────┐
│ The implantation alignment tool is then applied over the K-wire and positioned │
│ within the hole boundaries.                                                 │
└─────────────────────────────────────────────────────────────────────────────┘
                                      ↓
┌─────────────────────────────────────────────────────────────────────────────┐
│ The surgical cutter is applied over the implantation alignment tool and the hole is │
│ enlarged to its final dimensions, while the tool is oriented to be perpendicular to the │
│ articular surface.                                                          │
└─────────────────────────────────────────────────────────────────────────────┘
                                      ↓
┌─────────────────────────────────────────────────────────────────────────────┐
│ The alignment rod and the cutter are removed from the site; optionally the K-wire is │
│ removed;                                                                    │
└─────────────────────────────────────────────────────────────────────────────┘
                                      ↓
┌─────────────────────────────────────────────────────────────────────────────┐
│ A reamer is used to adjust the depth of the hole.                           │
└─────────────────────────────────────────────────────────────────────────────┘
                    ↙                                        ↘
┌───────────────────────────────────────┐   ┌───────────────────────────────────────┐
│   When a cannulated implant is used: │   │   When a non-cannulated        │
│ A smoothing tool is applied, positioned │   │       implant is used:         │
│ over the K-wire, the implant site is  │   │ A smoothing tool is applied, the hole is │
│ shaped and its final depth measured and│   │ shaped, the implant site is shaped and │
│ the smoothing tool is withdrawn;      │   │ its final depth measured and the     │
│ optionally the K-wire is removed      │   │ smoothing tool is withdrawn          │
│ (including via use of an adaptor) and a│   │                                      │
│ rod-like structure such as a K-wire   │   │                                      │
│ having a narrower diameter is inserted│   │                                      │
│ into the implantation site, optionally│   │                                      │
│ inserting within tissue underlying the│   │                                      │
│ implant site                          │   │                                      │
└───────────────────────────────────────┘   └───────────────────────────────────────┘
                    ↓                                        ↓
┌───────────────────────────────────────┐   ┌───────────────────────────────────────┐
│ The implant is then introduced over   │   │ The implant is then introduced        │
│ the K-wire                            │   │                                       │
└───────────────────────────────────────┘   └───────────────────────────────────────┘
```

Figure 14

TOOLS AND SYSTEMS FOR SOLID FORM AND GRAFT IMPLANTATION

CROSS REFERENCE TO RELATED APPLICATIONS

This application is a continuation of U.S. application Ser. No. 14/441,985, 35 U.S.C. § 371 Date May 11, 2015, which is the U.S. National Phase of PCT/IL2013/050,925, filed Nov. 11, 2013. PCT/IL2013/050,925 claims the benefit of U.S. Provisional Application No. 61/725,046, filed on Nov. 12, 2012, which is incorporated by reference herein in its entirety.

BACKGROUND

The incidence of bone, cartilage and osteochondral disease and defects is on the rise. Damage to bone, cartilage or both results in a number of diseases or conditions, which can be quite severe and may provide limited treatment options for the afflicted subject.

The treatment of all bone and/or cartilage lesions, for example, depends on the patient's age and the extent of the lesion. Treatment options for patients first manifesting symptoms of such lesions may include non-surgical treatment or surgical treatment. Surgical procedures to treat the lesions include open or arthroscopic drilling, debridement, bone marrow stimulation, bone grafting, chondrocyte implantation and osteochondral grafts.

Solid or semi-solid forms of implants for cartilage and bone regeneration or repair are promising therapies and may comprise, for example: osteochondral allograft or autograft, synthetic bi-phasic implant, coral based Implant, bi-phasic implants that are composed of aragonite in a first phase and aragonite and hyaluronic acid in a second phase and others.

Such implants for bone and cartilage regeneration or repair are often in use to treat cartilage, osteochondral and bone defects in the knee, ankle, shoulder, hip, elbow, vertebra etc.

Often when inserting such solid or semi-solid implants into a void, breakage of the implant may occur, due to the brittle nature of the material. For example, coral based implants or osteochondral autografts/allografts, are often fragile and should be handled with extreme caution when inserted into voids in a tissue.

To facilitate introduction of the solid forms within tissue, generally, a hole or void is first created within the tissue, for example within the bone, preferably with a diameter similar or slightly smaller than the area in which the implant is to occupy, ensuring a tight fit within the implant region. Such hole or void is typically introduced via drilling, with the obvious limitation of heating tissue proximal to the implantation site, compromising the same in terms of its healing capacity, or via manual manipulation, which can lead to obvious irregularities in terms of the void creation geometry, loss of appropriate orientation and the introduction of greater human error and thereby potential damage to the surrounding tissue at the insertion site.

In order to avoid dislodging of the implant, insertion to form a tight fit within the void is essential.

While many systems for implanting solid forms have been developed, including for osteochondral implants, none of the tools and systems is optimally and broadly applicable across the various fields of use for such solid implant forms. Furthermore, none prevent the care that must be exercised when implanting solid, yet somewhat fragile implants, and therefore breakage and/or suboptimal implantation of such implants can occur.

The success of grafting (implanting) depends on, among other factors, the fit in size and shape of the harvested graft (osteochondral plug) to the hole formed at the receiving site.

It is therefore necessary to have a tool or system for implanting solid forms or grafts, capable of being easily inserted into a void in the desired tissue, insertion with the correct orientation, without breakage during the press-fit insertion process and capable of being firmly attached to the appropriate corresponding structure, and in the desired depth relatively to the articular surface providing for integration of the implant within the tissue structure.

SUMMARY OF THE INVENTION

This invention provides, in one embodiment, an implantation alignment tool comprising:
  an elongated body having a central hollow spanning the length of said elongated body;
  a stabilization structure terminally joined to said elongated body by a joint region having a central hollow and further comprising:
    a first region comprising a first diameter, which first diameter is smaller than a diameter of said elongated body; and
    a second region having a second diameter, which second diameter is smaller than a diameter of said elongated body and larger than said first diameter,
    wherein said second region is sized to be of a dimension to facilitate a snug fit within the borders of a site of implantation.

In some embodiments, the elongated body has a varying outer diameter, varying inner diameter or a combination thereof along the length of said elongated body. In other embodiments, the elongated body has an outer diameter, inner diameter or a combination thereof that does not vary along the length of said elongated body.

In some embodiments, the at least a portion of a first region, at least a portion of a second region or a combination thereof contact a boundary of an implantation site.

In some embodiments, the first region is proximal to said joint region and said second region is proximal to said first region and distal to said joint region.

In some embodiments, the stabilization structure comprises alternating first and second regions arranged in a desired pattern such that a second region is located at a distal terminus of said stabilization structure.

In some embodiments, the second region contains at least one terminally extending scoring protrusion.

In some embodiments, the stabilization structure comprises alternating first and second regions along a horizontal axis of said stabilization structure.

In some embodiments, the stabilization structure comprises alternating first and second regions along a vertical axis of said stabilization structure.

In some embodiments, the stabilization structure comprises alternating first and second regions resembling a screw structure.

In some embodiments, the stabilization structure comprises alternating first and second regions resembling a drill bit structure.

In some embodiments, the elongated body comprises a material that is a metal, metal alloy, ceramic, glass or plastic.
In some embodiments, the stabilization structure comprises a metal, metal alloy, ceramic, glass or plastic and may optionally incorporate a flexible or shock-absorbing material.

In some embodiments, the stabilization structure and elongated body are comprised of the same material. In some embodiments, the stabilization structure and elongated body are formed as a single piece, for example, via cast molding, and other known means. In some embodiments, the the stabilization structure and elongated body are formed as separate pieces joined seamlessly together, for example, via welding, or other known means.

In some embodiments the alignment tool is adapted to fit over a rod-like structure.

In some embodiments, this invention provides a kit comprising an implantation alignment tool as herein described In some embodiments, the kit further comprises a surgical cutter, optionally adapted to fit over the implantation alignment tool in situ, wherein the alignment tool maintains a desired orientation of the surgical cutter during tissue harvest.

In some embodiments, the surgical cutter comprises at least one laterally extending protrusion, which may optionally be moved from an undeployed to deployed position, which at least one laterally extending protrusion may extend into the tissue walls proximally located to the defect site. In some embodiments, such surgical cutter may be further adapted to comprise markings or an adaptation so that the user may readily measure the dimensions of the implantation site boundaries, for example, depth, or sides, which in some embodiments, allows for user control to ensure the likelihood that the dimensions of the prepared implantation site are appropriate.

In some embodiments, the kit further comprises one or more rod-like structures. In some embodiments, the one or more rod-like structures may vary in terms of their composition, length, diameter or a combination thereof.

In some embodiments, the kit further comprises a surgical reamer, adapted to fit over the rod-like structure.

In some embodiments, the kit further comprises a surgical smoother, optionally adapted to fit over said implantation alignment tool in situ, or over a rod-like structure.

In some embodiments, the kit further comprises:
a drill bit assembly unit suitable for drilling tissue comprising:
a substantially hollow drill bit comprising a drilling region at a first terminus and a body region, wherein said body region comprises at least one lateral extension therefrom at a region distal to said first terminus; and
a substantially hollow drill bit protective sheath comprising a first region sized to accommodate insertion and permit free rotation of said drill bit around a longitudinal axis and a second region sized to prevent further advancement of said at least one lateral extension of said drill bit beyond a set point,
wherein when said second region engages said at least one lateral extension, advancement of said drill bit along a longitudinal axis is limited.

In some embodiments, the kit further comprises an implantation tool stabilizing implement comprising:
a hollow elongated body adapted for insertion of a rod-like structure therethrough; and
at least one stabilizing contact structure comprising an at least partially circular concave single piece structure having an inner tissue contact surface and an outer visualization surface, and an aperture adapted for insertion of said rod-like structure therethrough located centrally within said structure spanning said inner and outer surfaces.

In some embodiments, this invention provides an implantation tool stabilizing implement comprising:
a hollow elongated body adapted for insertion of a rod-like structure therethrough; and
at least one stabilizing contact structure comprising an at least partially circular concave structure having an inner tissue contact surface and an outer visualization surface, and an aperture adapted for insertion of said rod-like structure therethrough located centrally within said structure spanning said structure.

In some embodiments, the hollow cylindrical body is sized to accommodate insertion of a K-wire therethrough. In some embodiments, the diameter of the hollow cylindrical body in comparison to a diameter of the rod-like structure is such that the rod-like structure insertion therethrough leaves a space between an outer surface of the rod-like structure and an internal surface of said hollow cylindrical body.

In some embodiments, the stabilizing implement further comprises an adapter, which adapter possesses a diameter which is smaller than that of said hollow cylindrical body and which diameter is larger than a diameter of said rod-like structure and wherein said adapter is placed within said hollow cylindrical body and said rod-like structure may be inserted therethrough.

In some embodiments, the at least partially circular concave structure is comprised of a transparent or translucent material. In some embodiments, the hollow elongated body and said at least one stabilizing contact region are comprised of a metal, metal alloy, glass or plastic. In some embodiments, the hollow cylindrical body and said at least one stabilizing contact region are comprised of a different material. In some embodiments, the hollow cylindrical body is comprised of a metal or metal alloy. In some embodiments, the hollow cylindrical body is comprised of a plastic or glass. In some embodiments, the hollow cylindrical body and said at least one stabilizing contact region are comprised of the same material.

In some embodiments, this invention provides an implantation scoring tool comprising:
a longitudinal body which is optionally hollow and optionally adapted for insertion of a rod-like structure therethrough; and
at least one laterally extending protrusion, which protrusion is oriented substantially perpendicularly to a long-axis of said longitudinal body, optionally wherein said laterally extending protrusion optionally possesses a deployed and a compact position;
wherein when said implantation scoring tool is placed within an implant site and said laterally extending protrusion is in its deployed position, said laterally extending protrusion inserts within a tissue wall bounding said implant site thereby scoring said tissue wall.

In some embodiments, this invention provides a graft or solid implant introducing tool suitable for the introduction of brittle grafts or solid implants, said graft or solid implant introducing tool comprising:
a piston assembly containing a substantially elongated body, which optionally contains a hollow through which a rod-like structure may insert and a first terminus comprised of a shock-absorbent material and an advancer structure located at a second terminus of said substantially elongated body; and
a sheath which sheath accommodates insertion of said piston assembly therewithin, which sheath comprises:

an insertion region for insertion of said piston assembly;
a substantially hollow substantially cylindrical body into which said piston assembly may insert;
optionally a stopper region located proximally to said piston assembly when said piston assembly is inserted within said substantially hollow substantially cylindrical body, wherein said stopper region comprises a solid boundary containing an opening, which opening accommodates insertion of only a portion of said first terminus of said piston assembly;
optionally a stopper indicator region located proximally to said a graft or solid implant containment part, which indicator region may comprise a mark identifying optimal advancement of the graft or solid implant; and
a graft or solid implant containment part located proximally to said solid boundary of said stopper region, which part is comprised of a flexible shock-absorbing material and which part is optionally sized to accommodate insertion of only a portion of a graft or solid implant therewithin or which part will abut placement of said graft or solid implant placed proximally thereto.

In some embodiments, the stopper indicator region may include identifying marks on both the graft or solid implant containment part and on the sheath, and their alignment or combined configuration identifies optimal placement of said graft or implant. In other embodiments, the sheath may comprise a "window" or visible region such that when said the graft or solid implant containment part and achieves a desired advancement therewithin, visualization of the containment part within the window, or visualization of a symbol within such window serves as the identifying mark.

In some embodiments, this invention provides a graft or solid implant introducing tool suitable for the introduction of brittle grafts or solid implants, said graft or solid implant introducing tool comprising:
a substantially elongated body, which optionally contains a hollow extending therethrough, sized to accommodate insertion of a rod-like structure;
a first terminus comprised of a shock-absorbant material; and
an advancer structure located at a second terminus of said substantially elongated body; and
optionally a gripping part comprised of a flexible shock-absorbing material and which gripping part is sized to accommodate insertion of only a portion of a graft or solid implant therewithin; and/or
optionally a rod-like structure extending through said hollow in said substantially elongated body.

According to this aspect, and representing certain embodiments of this invention, a graft or implant is placed within a gripping part of a piston assembly, or, in some embodiments, within a gripping part of the graft or solid implant introducing tool, and the tool advances the implant or graft within an implantation site.

According to this aspect, and representing certain embodiments of this invention, a graft or implant is cannulated, or in some embodiments, comprises a void along a longitudinal axis spanning a length of such graft or implant, which graft or implant may then be threaded onto a rod-like structure.

In some aspects, such rod-like structure is itself threaded through the solid implant introducing tools of this invention, and the graft or implant abuts the first terminus or is contained within a gripping part of located at the first terminus of the solid implant introducing tool. According to one aspect of this embodiment, such rod-like structure is implanted within a tissue containing a prospective implantation site, and said graft or implant and the solid implant introducing tool are both threaded onto the rod-like structure in situ, whereby the advancing part of the solid implant introducing tool is used to advance the graft or implant to create an appropriate fit of the graft or implant within the implant site.

In some embodiments, the most terminal part of said gripping part is inserted into a void into which said graft or solid implant is to be inserted, and wherein said most terminal part of said gripping part is substantially flat and smooth. In some embodiments of the graft or solid implant introducing tool, the insertion region for insertion of the piston assembly, the substantially hollow body, stopper region, graft or solid implant containment gripping part or a combination thereof comprise a void such that said rod-like structure may insert therethrough.

In some embodiments, the substantially elongated body of said piston assembly, said insertion region for insertion of said piston assembly, said substantially hollow substantially cylindrical body, said stopper region or a combination thereof are comprised of a glass or plastic.

In some embodiments, the first terminus of said piston assembly, gripping part or a combination thereof is comprised of a silicon, rubber or latex material.

In some embodiments, this invention provides solid implants comprising a hollow along a longitudinal axis of such implant, which may be adapted to fit over a rod-like structure as herein described.

This invention provides a kit comprising the implantation tool stabilizing implement as herein described. In some embodiments, this invention provides a kit comprising an implantation alignment tool as herein described. In some embodiments, this invention provides a kit with any one or more tools as herein described in any combination, as will be appreciated by the skilled artisan.

This invention also provides a method of tissue implantation in a subject, which method minimizes damage to an area of tissue implantation, said method comprising the steps of:
inserting a rod-like structure within a target tissue implantation site in a subject, optionally with the aid of an implement orienting said rod-like structure to be in an orientation perpendicular to a plane of a surface of said target graft withdrawal or implantation site and in an orientation to be centralized within said implantation site;
drilling an area of tissue in said subject which is less than that of a desired tissue implantation site in an orientation perpendicular to a surface of said area of tissue, optionally with a drill bit adapted for application over said rod-like structure;
applying the implantation alignment tool of claim 1 over said rod-like structure and positioning same within said area of tissue;
surgically excising tissue from an area of desired implantation, by optionally applying a surgical cutter over said implantation alignment tool of claim 1; and
applying a tissue graft or solid implant within said area of tissue, optionally by inserting a cannulated implant within said site, over said rod-like structure
wherein drilling in an orientation perpendicular to a surface of the target tissue and subsequent application of said surgical cutter over said implantation alignment tool to surgically excise desired tissue from said area of tissue for implantation in said subject minimizes damage to an area of tissue implantation in said subject.

This invention also provides a method of tissue graft extraction in a subject, which method minimizes damage to an area of tissue in said graft and tissue surrounding said graft extraction site, said method comprising the steps of:

inserting a rod-like structure within a target graft withdrawal site in a subject, optionally with the aid of an implement orienting said rod-like structure to be in an orientation perpendicular to a plane of a surface of said target graft withdrawal and in an orientation to be centralized within said target graft withdrawal site;

drilling an area of tissue in said subject which is less than that of a desired graft extraction site in an orientation perpendicular to a surface of said area of tissue, optionally with a drill bit adapted for application over said rod-like structure;

applying an implantation alignment tool as herein described over said rod-like structure and positioning same within said area of tissue; and surgically excising tissue from an area of desired graft extraction, by optionally applying a surgical cutter over said implantation alignment tool;

wherein drilling in an orientation perpendicular to a surface of the target tissue and subsequent application of said surgical cutter over said implantation alignment tool to surgically excise desired tissue from said graft site in said subject minimizes damage to an area of tissue to an area of tissue in said graft and tissue surrounding said graft extraction site.

This invention provides a method for minimizing damage to an area of solid implant insertion in a tissue in a subject in need thereof, said method comprising the steps of:

inserting a rod-like structure within an implantation site in a subject with the aid of an implement orienting said rod-like structure to be in an orientation perpendicular to a plane of a surface of said target implantation site;

applying an implement comprising a terminally located drill bit over said rod-like structure and drilling an area of tissue in said subject which is less than that of a desired implantation site, which implement is optionally said implantation alignment tool, which in some embodiments may comprise further terminal modification to approximate a drill-bit or screw-like structure, which in some embodiments facilitates more stable incorporation of the tool within the desired implantation site and neighboring tissue thereto, and optionally wherein said implement is positioned within a drill bit protective sheath, thereby minimizing damage to tissue located proximally to said area of tissue in said subject and optionally removing said implement;

optionally applying the implantation alignment tool over the rod-like structure;

applying a surgical cutter over said rod like structure or said implantation alignment tool and surgically excising desired tissue from said area of implantation which is equal to or slightly smaller in size than that of a desired implantation site to ensure press-fit therewithin;

optionally applying a tissue reamer adapted to fit over a rod-like structure or said implantation alignment tool, to enlarge the implantation site, which reamer optionally contains markings indicating a depth of insertion;

optionally applying a smoothing tool over said rod-like structure or said implantation alignment tool and surgically smoothing said area of tissue in said implantation site; and applying a tissue graft or solid implant within said area of tissue.

wherein insertion of said drill bit over said rod-like structure for minimal drilling in a tissue ensures optimized drilling in an orientation perpendicular to a surface of the target tissue and applying said surgical cutter over said stabilizing structure and surgically excising desired tissue from said area of desired solid implantation to an area of tissue in said subject ensures that minimal damage occurs to an area of solid implant insertion in said tissue and optimal orientation of solid implant insertion or a combination thereof is achieved In some embodiments, the method further comprises the steps of:

applying an implantation tool stabilizing implement to a surface of a target implantation site in a subject, wherein said implantation tool stabilizing implement comprises:

a hollow elongated body adapted for insertion of a rod-like structure therethrough; and at least one stabilizing contact structure comprising an aperture adapted for insertion of said rod-like structure therethrough, and an at least partially circular concave single piece structure having an inner tissue contact surface and an outer visualization surface, establishing a stabilized application of said implantation tool stabilizing implement such that insertion of said rod-like structure therewithin will be in an orientation perpendicular to a plane of said surface of a target implantation site and affixing said rod like structure within tissue of an area of desired solid implantation;

inserting said implement comprising a terminally located drill bit over said rod-like structure, drilling said area of tissue, optionally removing said drill bit, applying said implantation alignment tool and said surgical cutter and surgically excising said desired tissue;

removing said surgical cutter, said implantation tool alignment implement and said rod-like structure from said area of desired solid implantation;

optionally scoring lateral walls bounding said area of desired solid implantation; and inserting a solid implant within said area of desired solid implantation by applying a graft or solid implant to form a tight fit within said area of desired solid implantation

BRIEF DESCRIPTION OF THE DRAWINGS

FIG. 1 (A-H) schematically depict embodiments of an implantation tool stabilizing implement of this invention.

FIG. 2 (A-F) schematically depict embodiments of an implantation tool stabilizing implement of this invention and for use in the methods of this invention, containing multiple stabilizing contact structures in different embodied configurations.

FIG. 3 (A-E) schematically depict schematically depicts different components of embodied tools of this invention for use in the kits and methods of this invention, for example, rod-like structures, an embodied drill bit assembly including the insertion of a rod-like structure therethrough and an embodied drill bit protective sheath.

FIG. 4 (A-I) schematically depict embodiments of implantation alignment tools of this invention for use in the kits and methods of this invention.

FIG. 5 (A-J) schematically depict embodiments of implantation alignment tools of this invention and for use in the kits and methods of this invention showing multiple embodied stabilization structures in different embodied configurations. Further terminal modifications including lateral protrusions are envisioned.

FIG. 6 (A-D) schematically depict embodiments of surgical cutters of this invention and for use in the kits and methods of this invention.

FIG. 7 (A-G) schematically depict embodiments of reamers and smoothing tools of this invention and for use in the kits and methods of this invention.

FIG. 14 provides a flow chart illustrating an embodied procedure for introducing a graft or solid implant into a subject, making use of the tools of this invention.

DESCRIPTION OF THE INVENTION

Figure 8D:
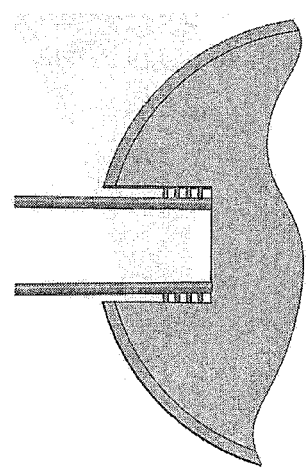
FIG. 8 (A-D) schematically depict embodiments of implantation scoring tools of this invention including depicting a collapsed and deployed state of the embodied scoring tool.
Figure 8C:
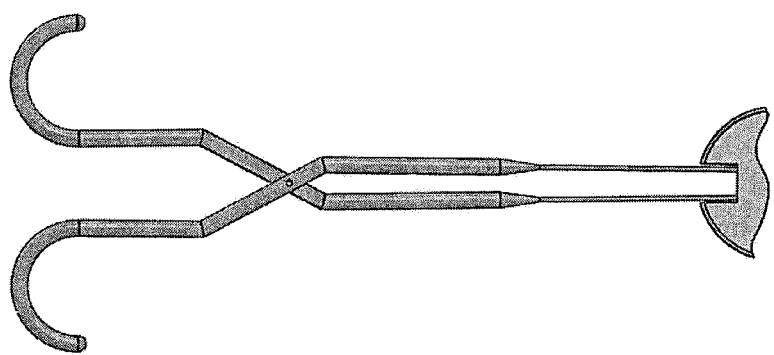
Figure 8B:
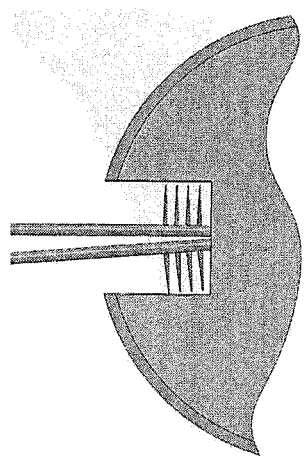
Figure 8A:
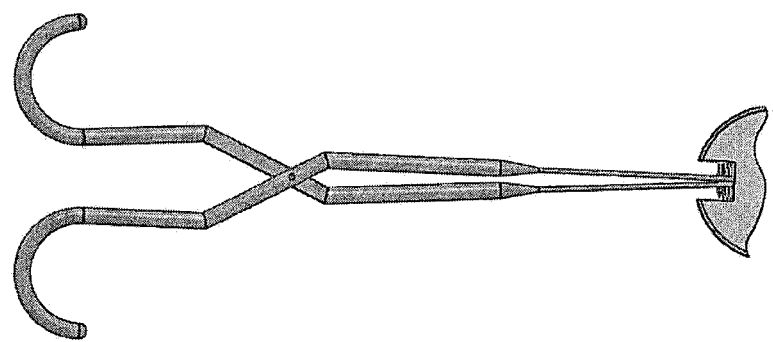

This invention provides tools and kits for removal of a graft and/or for integration of a solid or semi-solid form implant or graft implant within an appropriate desired tissue minimizing the potential for or actual breakage of the implant or graft during the stated process.

A fundamental problem in the field of graft and solid implant insertion within a desired tissue site is that improper insertion of the same leads to incomplete healing and suboptimal function to loss of function, depending upon the nature and severity of the inappropriate insertion. This problem in particular is encountered when implanting a solid form within or when traversing bone tissue.

In some embodiments, the tools, kits and methods provide for a much more oriented application of the implant, and a means for both extracting and implanting matter within or traversing bone tissue, which preserves greater viability and intact structure of the tissues (bone and cartilage) affected as part of these procedures.

In some embodiments, the invention provides methods for minimizing damage to an area of tissue graft extraction in a subject in need thereof, for minimizing damage to an area of solid implant insertion in a tissue in a subject in need thereof, and/or for optimizing the orientation of a solid implant or graft insertion in a subject in need thereof.

In some embodiments, the invention for the first time provides a means for ideal creation of a void within solid tissue such as bone and cartilage, whereby the viability of the cells and integrity of the solid tissue into which an implant is inserted is significantly preserved, or at least much more minimally affected.

In some embodiments, typically procedures for creation of a void within solid tissue, which in turn precedes an implantation procedure are marked by damage to the structure of the solid, e.g. bone and cartilage tissues for the extraction and implantation steps. Typical extraction methods entail use of either automated tools such as a drill to provide access to the bone tissue, or involve manual means for accessing the same.

Surprisingly, by creating a new tool and tool system, it has been found that the two traditional methods of automated and manual access of the bone and/or cartilage can be combined in a manner that preserves ideal orientation of the tools, thereby providing for optimal results, wherein the viability of the cells and integrity of the solid tissue into which an implant is inserted is significantly preserved, or at least much more minimally affected.

Other embodied and contemplated advantages of the tools, kits and methods of this invention include, but are not limited to a means for drilling a diameter within the target tissue, which ensures creation of a void or hole coupled with subsequent manual tissue cutting, ensuring that any damage to a region of the target tissue as a result of the drilling process is limited and at a distance from the implant region walls and so prevents heating/necrosis/wobbling which can cause damage to the adjacent tissue. This in turn prevents significant cell and tissue death, which would defect the desired effect of tissue repair and regeneration as part of the implant incorporation. Furthermore, and representing another contemplated advantage, such a systematic approach limits the potential for poor shaping of the boundaries of the tissue into which the implant is inserted and promotes the ability to achieve press fit insertion of the implant.

This invention provides a method of tissue implantation in a subject, which method minimizes damage to an area of tissue implantation, said method comprising the steps of:
  inserting a rod-like structure within a target tissue implantation site in a subject, optionally with the aid of an implement orienting said rod-like structure to be in an orientation perpendicular to a plane of a surface of said target graft withdrawal or implantation site and in an orientation to be centralized within said implantation site;
  drilling an area of tissue in said subject which is less than that of a desired tissue implantation site in an orientation perpendicular to a surface of said area of tissue, optionally with a drill bit adapted for application over said rod-like structure;
  applying the implantation alignment tool of claim 1 over said rod-like structure and positioning same within said area of tissue;

surgically excising tissue from an area of desired implantation, by optionally applying a surgical cutter over said implantation alignment tool of claim 1; and applying a tissue graft or solid implant within said area of tissue, optionally by inserting a cannulated implant, or in some embodiments, an implant containing a void along an axis spanning a length of such implant, within said site, over said rod-like structure wherein drilling in an orientation perpendicular to a surface of the target tissue and subsequent application of said surgical cutter over said implantation alignment tool to surgically excise desired tissue from said area of tissue for implantation in said subject minimizes damage to an area of tissue implantation in said subject.

This invention also provides a method of tissue graft extraction in a subject, which method minimizes damage to an area of tissue in said graft and tissue surrounding said graft extraction site, said method comprising the steps of:

inserting a rod-like structure within a target graft withdrawal site in a subject, optionally with the aid of an implement orienting said rod-like structure to be in an orientation perpendicular to a plane of a surface of said target graft withdrawal and in an orientation to be centralized within said target graft withdrawal site;

drilling an area of tissue in said subject which is less than that of a desired graft extraction site in an orientation perpendicular to a surface of said area of tissue, optionally with a drill bit adapted for application over said rod-like structure;

applying the implantation alignment tool of claim 1 over said rod-like structure and positioning same within said area of tissue; and surgically excising tissue from an area of desired graft extraction, by optionally applying a surgical cutter over said implantation alignment tool of claim 1;

wherein drilling in an orientation perpendicular to a surface of the target tissue and subsequent application of said surgical cutter over said implantation alignment tool to surgically excise desired tissue from said graft site in said subject minimizes damage to an area of tissue to an area of tissue in said graft and tissue surrounding said graft extraction site.

This invention still further provides a method for minimizing damage to an area of solid implant insertion in a tissue in a subject in need thereof, said method comprising the steps of:

inserting a rod-like structure within an implantation site in a subject with the aid of an implement orienting said rod-like structure to be in an orientation perpendicular to a plane of a surface of said target implantation site;

applying an implement comprising a terminally located drill bit over a rod-like structure and drilling an area of tissue in said subject which is less than that of a desired implantation site, or applying an implantation alignment tool as herein described, which tool comprises a terminal modification to approximate a drill bit, or screw-like structure, or structure approximating a structure commonly associated with a screwdriver tool, for example, a "Phillips head" type structure, or in some embodiments, any structure that facilitates creating a hole or void within the tissue to which the tool is applied, and optionally wherein said implement is positioned within a drill bit protective sheath, as herein described;

thereby minimizing damage to tissue located proximally to said area of tissue in said subject and optionally removing said implement;

optionally applying the implantation alignment tool of claim 1 over said rod-like structure;

applying a surgical cutter over said rod like structure or said implantation alignment tool of any one of claim 1, 8 or 9 and surgically excising desired tissue from said area of implantation which is equal to or slightly smaller in size than that of a desired implantation site to ensure press-fit therewithin;

optionally applying a tissue reamer adapted to fit over a rod-like structure or said implantation alignment tool, to enlarge the implantation site, which reamer optionally contains markings indicating a depth of insertion;

optionally applying a smoothing tool over said rod-like structure or said implantation alignment tool and surgically smoothing said area of tissue in said implantation site; and applying a tissue graft or solid implant within said area of tissue.

wherein insertion of said drill bit over said rod-like structure for minimal drilling in a tissue ensures optimized drilling in an orientation perpendicular to a surface of the target tissue and applying said surgical cutter over said stabilizing structure and surgically excising desired tissue from said area of desired solid implantation to an area of tissue in said subject ensures that minimal damage occurs to an, area of solid implant insertion in said tissue and optimal orientation of solid implant insertion or a combination thereof is achieved.

In some embodiments, the method for minimizing damage to an area of solid implant insertion in a tissue in a subject in need thereof, said method comprising the steps of:

inserting a rod-like structure within an implantation site in a subject with the aid of an implement orienting said rod-like structure to be in an orientation perpendicular to a plane of a surface of said target implantation site;

applying an implement comprising a terminally located drill bit over said rod-like structure, which implement is optionally said implantation alignment tool stabilization structure, which implement comprises a terminally located structure resembling a screw structure, or a drill bit or comparable structure, as described herein, and optionally wherein said implement is positioned within a drill bit protective sheath, drilling an area of tissue in said subject which is less than that of a desired implantation site, thereby minimizing damage to tissue located proximally to said area of tissue in said subject and optionally removing said implement;

optionally applying the implantation alignment tool as herein described over said rod-like structure, when said implantation alignment tool stabilization structure does not comprise a screw structure;

applying a surgical cutter over said implantation alignment tool as herein described and surgically excising desired tissue from said area of substantially desired solid implantation to an area of tissue in said subject which is equal to or slightly smaller than that of a desired implantation site to ensure press-fit therewithin;

applying a reamer tool which in turn is cannulated to accommodate insertion therethrough of said rod like structure or said implantation alignment tool, which facilitates ascertaining a depth of the tissue being cut within an implant site, and which optionally may comprise a guide or markings to designated a desired depth;

optionally applying a scoring tool to score the sides of the implant site to promote influx of blood and tissue products within a desired implant site;

applying a smoothing tool over said implantation alignment tool as herein described and surgically smoothing said area of tissue in said subject which is equal to that of a desired implantation site; and optionally applying a tissue graft or solid implant within said area of tissue.

wherein insertion of said drill bit over said rod-like structure for minimal drilling in a tissue ensures optimized drilling in an orientation perpendicular to a surface of the target tissue and applying said surgical cutter over said stabilizing structure and surgically excising desired tissue from said area of desired solid implantation to an area of tissue in said subject ensures that minimal damage occurs to an area of solid implant insertion in said tissue and optimal orientation of solid implant insertion or a combination thereof is achieved.

A similar method as herein described is used for a perpendicular positioning and minimizing damage to an area of tissue graft extraction in a subject in need thereof.

According to this aspect, and in some embodiments, the tools, kits and methods are particularly suitable for arthoscopic and minimally invasive procedures.

In some embodiments, the methods of this invention may further include the step of creating an opening in a region proximal to the bone or other solid tissue into which a graft or solid form is to be implanted, or from which a graft may be removed. For example, and as a non-limiting embodiment, methods for graft or solid form implantation within the knee may include a mini-arthrotomy procedure or an arthroscopy procedure to create an opening therein. Following the exposure of the implant site, the methods may, in some embodiments, make use of an implantation tool stabilizing implement for the extraction/removal of some tissue at the implant/graft site.

This invention provides, in one embodiment, an implantation tool stabilizing implement comprising:

at least one hollow elongated body adapted for insertion of a rod-like structure therethrough; and at least one stabilizing contact structure comprising an at least partially circular concave structure having an inner tissue contact surface and an outer visualization surface, and an aperture adapted for insertion of said rod-like structure therethrough located centrally within said structure spanning said inner and outer surfaces.

FIG. 1 (A-H)-FIG. 2 (A-F) depict embodied aspects of a stabilizing implement of this invention. According to one aspect, the stabilizing implement contains a hollow elongated body 10 adapted for insertion of a rod-like structure therethrough, for example, inserted within the void beginning at 20 and spanning the length of the body, for example, as noted by "E", the cross section of which is shown in FIG. 1C. The stabilizing implement further comprises a stabilizing contact structure 15, such that a rod-like structure may be inserted through the lumen of the tool and such rod-like structure spans the entire length of the tool inserting at the aperture at 20 and exiting an aperture 50. The line drawn from one "E" to another "E" in FIG. 1B may also serve to assist visualization of the insertion of the rod-like structure through the lumen of the tool. In this aspect, and one embodiment of the tool, the region of the body most proximal to the stabilizing contact structure 15 may be tapered 25 so that a narrower diameter is present. In other embodiments, however, the diameter spanning the stabilizing contact structure and elongated body is the same.

In some embodiments, the hollow elongated body 10 is substantially cylindrical in shape, but it will be appreciated that any elongated shape is envisioned. In some embodiments, the elongated body may be shaped to be ergonomically favorable for the hand of the user, including particular grasp regions thereupon, and in some embodiments, incorporating ergonomically favorable materials within and/or near such grasp regions, and such adaptations are envisioned, as well and are contemplated embodiments of this invention.

In some embodiments, the handles of the tools of this invention may be further constructed to comprise common grips as seen, for example, in existing handles for similar tools, for example, screw drivers, and the like.

In some embodiments, the stabilizing contact structure is comprised of a single piece, and in some embodiments, it is modular. In some embodiments, the stabilizing contact structure and elongated body are comprised of a single piece and in some embodiments, they are modular. In some embodiments, reference to components being "comprised of a single piece" refers to components cast molded, for example, or otherwise manufactured to assemble as such, or in some embodiments, such components may be prepared separately and seamlessly joined, for example via welding or appropriate other fixation methods, and still be considered to be "comprised of a single piece."

In some embodiments, the stabilizing contact structure and elongated body are constructed separately or comprised of components not of a single piece, and may be comprised of the same or different materials, as will be appreciated by the skilled artisan.

It is to be noted that any of the tools of this invention as described herein may have components comprised of a single piece and in some embodiments, the same may be modular. In some embodiments, reference to any components being "comprised of a single piece" refers to components cast molded, for example, or otherwise manufactured to assemble as such, to form a contiguous tool, or in some embodiments, such components may be prepared separately and seamlessly joined, for example via welding or appropriate other fixation methods, and still be considered to be "comprised of a single piece."

In some embodiments, any of the tools of this invention as described herein may have components constructed separately or comprised of components not of a single piece, and may be comprised of the same or different materials, as will be appreciated by the skilled artisan.

The methods of preparation of any of the tools of this invention may include any appropriate conventional method for the same, including machining, cast molding, lithography and milling, and other methods, as known in the field.

The tools, kits, and methods of this invention are particularly suitable for use with any graft or implant for extraction from and/or application to a subject, respectively, for example, as described in PCT International Publication Number WO 2010/146575, WO 2010/146574, WO 2010/058400, WO 2009/066283, all of which are incorporated by reference herein in their entirety.

In some embodiments, use of the stabilizing implements of this invention may additionally provide for an ability to measure the placement of the K-wire inserted therethrough, to ensure the centralized placement of the K-wire, and facilitate perpendicular alignment thereof.

Referring now to FIGS. 1E-1F, and representing another aspect, the region of the body most proximal to the stabilizing contact structure 15 may comprise a joint region 45 such that the stabilizing contact structure 15 may be removably attachable to a longitudinal body section 10. Such region 45 may also represent a removable and interchangeable part, in one aspect of this invention.

FIGS. 1G and 1H provide external and cross sectional views, respectively, showing a lumen 50, which does not vary in terms of its diameter, along the length of the tool.

The longitudinal body section may also comprise at least one connector 60. Such connector may be apically or basally located, for example as depicted in FIG. 2A versus FIG. 2B. Referring to FIG. 2A, and representing one embodiment of the invention, a stabilizing implement of this invention, wherein the longitudinal body section 10 contains a stabilizing contact structure containing part 45 having a first terminal region most proximally located to the stabilizing contact structure 15 and a second region which may be permanently or removably attached to a longitudinal body section 10. In this aspect, the stabilizing contact structure containing part 45 contains a proximal terminal region comprising laterally extending connectors 60, which in turn connect to second 65 and third 70 partial stabilizing implement units, comprising a joint region proximally located to a stabilizing contact structure 15, which joint region may be removably attachable to a longitudinal body section 10 (Paired FIGS. 2A and 2D, FIGS. 2B and 2E, and FIGS. 2C and 2F depict such removably attachable longitudinal body section insertion within said joint region).

Referring to FIGS. 2B and 2C, and representing one embodiment of the invention, a stabilizing contact structure may, in some embodiments, also comprise one or more connectors 60, which connector stably connects at least a first stabilizing contact structure 65 and at least a second stabilizing contact structure 70. As in the embodiments depicted in FIGS. 2A and 2D, the joint regions 60 may be removably attachable to a longitudinal body section 10 (FIGS. 2B, 2C and 2D, 2F, respectively, depict such removable attachment of the longitudinal body section 10 insertion within stabilizing contact structure containing part 45, whereby connectors 60 may be any form, whether permanently connected or removably connected).

In some embodiments, such connectors may comprise any known appropriate material and structure. For example, in some embodiments, such connectors may be in the form of a screw mechanism, snap mechanism, press fit, hook or tab insert, etc. In some embodiments, such connectors are permanently affixed, and in some embodiments, such connectors are removably attached, for example, modularly attached for expansion of the potential number of joined stabilizing contact structures to ensure optimal distribution of the implant/implants relative to the defect.

It is to be understood that the implements according to this aspect may comprise or be removably connected to an array of stabilizing contact structures and proximally located body sections or partial body sections. Such array may comprise any number or multiple of stabilizing contact structures and proximally located body sections or partial body sections, and any appropriate orientation for the same is envisioned and the examples shown in FIG. 2 should not be construed as limiting the invention in any way in terms of the multiple shown for the stabilizing contact structures and proximally located body sections or partial body sections (depicting in this case a multiple of 3 such structures) or orientation of the same (depicting in this case an array in a row or arranged around a central axis).

In some aspects, the entire outer rim of the stabilizing contact structure of the implement is fully in contact with the articular surface. Without being bound by theory, in some aspects, such structure facilitates perpendicular alignment of the implement with the articular surface to optimize implantation.

In some embodiments, the hollow cylindrical body region adapted for insertion of a rod-like structure therethrough is sized to accommodate insertion of a K-wire, and in some embodiments, the rod-like structure is any structure so-shaped and sized as to be appropriate for surgical insertion within a tissue, for example, screws, pins, molly or molly bolt or a drill bit, which may, for example, remain inserted, and any anchored version of the same, e.g. anchor, hook, or other similar structure, as will be appreciated by the skilled artisan.

In some embodiments, such structures may be comprised of a material reinforced plastic, stainless steel or other materials as herein described, as will be appreciated by the skilled artisan. In some embodiments, the material will be sufficiently sturdy so as to be appropriate for use in the types of procedures as described herein. In some embodiments, such material may be further transparent or translucent or otherwise provide markings to provide the user with a means of assessing placement and orientation.

In some embodiments, the implement is inserted, positioned and stabilized in a perpendicular orientation relative to the implantation location (articular surface). In some embodiments, once the orientation is achieved, a K-wire is threaded through the implantation tool stabilizing implement and anchored into the bone with a resulting perpendicular orientation relative to the articular surface.

When preformed arthroscopically a working channel or cannula or tube, etc. can be used. It will be appreciated by the skilled artisan that any appropriate structure may be used for such purpose. In some embodiments, the implantation tool stabilizing implement may comprise a stopper, which stopper prevents leakage/dispersion of fluid used in the implantation procedure.

According to one aspect of the invention, the tools of this invention are particularly suitable for use in tissue graft extraction and/or solid form or graft implantation. In one aspect, the tools of this invention are particularly suited for extraction and/or implantation of a brittle solid material from a tissue, and in some embodiments, access to the region of extraction and/or implantation may necessitate tool stabilization in order to ensure optimal extraction and/or implantation. In some embodiments, the tools of this invention are particularly useful for bone and/or cartilage graft extraction, and solid form implantation within bone or osteochondral defects.

In some embodiments, methods for the production of the tools as herein described are standard methods for producing related tools and reflect a consideration of the materials used and geometry desired in the tools.

For example, and in some embodiments, plastic and ceramic tools may employ the use of molds, etc.

In some embodiments, the implantation tool stabilizing implement is placed in an orientation with respect to a plane of the surface to which the implement is applied that is perpendicular thereto and is centralized within the defect site.

In some embodiments, the stabilizing contact structure comprises an at least partially circular concave single piece structure, suitable for placement proximally to an articular surface, and the contact structure serves the function of ensuring a desired orientation of the implement with respect to a plane of the target surface.

In some embodiments, the stabilizing contact structure may be constructed with varying diameters, which may correspond, in turn, with a size of a defect into which an implant will be inserted, or in some embodiments, which may correspond, in turn, with a size of a desired graft dimension, which may correspond, in turn, with a size of an implant or graft which will be inserted within a void created at or near the target surface.

In some embodiments, the stabilizing contact structure comprises visible markings or demarcations on its surface, which provide an indication regarding the measurement of the length, width and/or circumference of underlying material onto which the same is placed (see for example, FIGS. 1A, 1D, 35 etc.). Such demarcations, for example, are useful in providing a concrete assessment of the size of the defect and/or the size of implant needed in accordance with the methods of this invention, and serving as certain embodiments thereof.

In some embodiments, the implantation tool stabilizing implement may be considered to be a cannulated tool, having a rod-like structure, such as a K-wire threaded therethrough.

In some embodiments, the inner diameter of the implantation tool stabilizing implement, including the inner diameter of the partially hollow cylindrical body insertion region, longitudinal body section and/or stabilizing contact structure is sized to fit for the insertion of a rod-like structure such as a K-wire of a given diameter, along the entire length of the implantation tool, i.e. the rod like structure inserts at an apex and spans the entire length of the tool, exiting therethrough at a base of the tool. In some embodiments, the insertion region adapted for insertion of a rod-like structure therethrough is located proximally to said at least one stabilizing contact structure. In some embodiments, the insertion region adapted for insertion of a rod-like structure therethrough is located distally to said at least one stabilizing contact structure.

In some embodiments, the implementation tool may be sized such that a diameter of the tool is significantly larger than the diameter of the rod-like structure inserted therethrough. According to this aspect, and in some embodiments, the implementation tool may further incorporate an adapter, can be full or partial, for example, in some embodiments, the adapter may span a short length at the top of the tool, or the bottom of the tool, or in some embodiments, the adapter may span the length of the tool lumen. In some embodiments, such adapter may be comprised of flexible or non-flexible material, however care is taken to prevent lateral movement of the wire within the adapter.

In some embodiments, according to this aspect, the implantation tool stabilizing implement further comprises an adapter, which adapter possesses a diameter which is smaller than that of said partially hollow cylindrical body insertion region and which diameter is larger than a diameter of said rod-like structure and wherein said adapter is placed within said partially hollow cylindrical body insertion region and said rod-like structure may be inserted therethrough.

In some embodiments, the diameter of the insertion region in comparison to a diameter of the rod-like structure is such that the rod-like structure insertion therethrough leaves minimal space between an outer surface of the rod-like structure and an internal surface of said insertion region.

In some embodiments, the at least partially circular concave single piece structure is comprised of a transparent or translucent material.

In some embodiments, according to this aspect, the use of transparent or translucent material, such as plastics or glasses render the underlying tissue, for example, target cartilage and bone tissue and the harvest/lesion site to be visible, facilitating optimal, centered implantation or harvest, based on the central positioning of the tool. According to this aspect, and in some embodiments, when using a transparent polymer the target tissue, such as cartilage, is visible and the positioning of the implement on, for example, the articular surface located proximally thereto may be clearly seen, which positioning assures stable positioning of the implant and ultimately leading to ideal graft retrieval and/or implant/graft insertion. In some embodiments, the material may comprise silicon, plastic, or a polymeric material.

In some embodiments, the material may be opaque, but with certain sections, which are partially exposed, for example, spaced holes in the opaque material, which allows visualization of what is placed through the lumen of the same, thereby being effectively transparent even when employing a solid material.

In some embodiments, according to this aspect, the at least partially circular concave single piece structure is comprised of an opaque material.

In some embodiments, according to this aspect, the at least partially circular concave single piece structure comprises an exposed circular scale bar, which scale bar facilitates the measurement of the diameter of the defect serving as the implantation site, and/or the diameter of the graft tissue being isolated (see for example, FIGS. 1A, 1D, 35 etc.). According to this aspect and in some embodiments, visualization of the size of implant or graft site is facilitated when the at least partially circular concave single piece structure comprising such a scale bar is comprised of a transparent or translucent material.

In some embodiments, according to this aspect, the scale bar facilitates the optimal choice in implant/graft diameter size, and in some embodiments, for example, such choice may also reflect use of multiple implants/grants and the ability to provide for the optimal distribution of the same within a target site.

In some embodiments, according to this aspect, the least one hollow cylindrical body and at least one stabilizing contact region are comprised of the same material. In some embodiments, according to this aspect, the at least one hollow cylindrical body and at least one stabilizing contact region are comprised of a metal, metal alloy, polymers, silicon, ceramic, glass or plastic.

In some embodiments, according to this aspect, the at least one hollow cylindrical body and at least one stabilizing contact region are comprised of different materials.

In some embodiments, according to this aspect, the at least one hollow cylindrical body is comprised of a metal or metal alloy or a ceramic. In some embodiments, according to this aspect, the at least one partially hollow cylindrical body insertion region is comprised of a plastic or glass or any method as described for use in connection with another tool of this invention.

In some embodiments, according to this aspect, the invention provides a kit comprising an implantation tool stabilizing implement of this invention.

The insertion of a rod-like structure through the implantation tool stabilizing implements of this invention during an implantation or graft harvest procedure enables optimal, consistent orientation of the tools for use in such procedures and in some embodiments, greater control of the depth of advancement of certain tools used in such procedures is provided. According to this aspect, and in some embodiments, the rod-like structure may be so constructed as to contain indicator marks indicating the depth of insertion of the rod-like structure within a graft isolation/implantation site, for example, and in some embodiments, the rod-like structure may contain laser marks to indicate the depth of insertion of the same.

In some embodiments, this invention provides a drill bit protective sheath, comprising:
  a first hollow region along an internal longitudinal axis of said protective sheath, which hollow region is sized to accommodate insertion of said drill bit, whereby said hollow region is sized to permit free rotation of said drill bit around a longitudinal axis; and
  a second region sized to accommodate insertion of at least one lateral extension of a drill bit,
wherein when said second region engages said at least one lateral extension of a drill bit, advancement of said drill bit along a longitudinal axis is limited.

In some embodiments, the drill bit assembly unit may contain markings or set extension intervals such that advancement beyond a certain point is readily seen or prevented, providing a means to set a desired drilling depth.

In some embodiments, this invention provides a drill bit assembly unit suitable for drilling tissue, said drill bit assembly comprising:
  a drill bit comprising:
    a substantially hollow drill bit comprising a drilling region at a first terminus, a body region and at least one lateral extension from said body at a region distal to said first terminus; and optionally
    a drill bit protective sheath as herein described.

In some embodiments, the drill bit and/or drill bit protective sheath is comprised of a glass, plastic, metal or metal alloy material, or in some embodiments, can be made of different materials, as will be appreciated by the skilled artisan.

In some embodiments, the invention contemplates providing a drill bit or drill bit protective sheath as herein described alone, or in a kit of parts.

In some embodiments, according to this aspect, following removal of the implement from being positioned over the rod-like structure, a drill bit assembly is positioned appropriately and used, for example, to gain access to the underlying target tissue for a graft procedure or in some embodiments, for shaping an implantation site more optimally in order to best incorporate an implant.

According to this aspect, and in one embodiment, a drill bit protective sheath is placed over the rod-like structure and the drill bit is inserted therein, over the rod-like structure and within the protective sheath and attachment of the assembly to an appropriate drill. In some embodiments, the drill bit is placed over the rod-like structure followed by fitting of the drill bit protective sheath over the drill bit and attachment of the assembly to an appropriate drill. Upon commencement of drilling, the drill bit is advanced within the target tissue site, optionally and in some embodiments, to a depth regulated by the stopper mechanism described hereinabove.

Referring to FIG. 3 (A-E), an embodied rod-like structure 75 (FIG. 3A) is shown. Such rod-like structure may be positioned internally to a drill bit 85 (FIG. 3B, with a cross section of the bit being at "F" shown in FIG. 3C). The drill bit may comprise at least one lateral extension 80, which, in one embodiment, when fitted within the drill bit protective sheath 90 (FIG. 3D depicts the sheath, with cross section at "G" being depicted in FIG. 3E) within the fitted containment region of the sheath 95, the engagement of the lateral extension of the drill bit with the fitted containment part constitutes a stopper mechanism.

As will be appreciated, the drill bit in accordance with this aspect may be considered to be a cannulated drill bit, accommodating the insertion of a rod-like structure therewithin.

In some embodiments, the drill bit protective sheath comprises a part of a stopper mechanism facilitating regulation of the drill depth achieved, and safeguarding against drilling beyond a desired depth. In other embodiments, the drill bit protective sheath further aids in prevention of or mitigation of any damage to target tissue at the drilling region, for example by protecting the same from direct contact with a rotating drill bit. In some embodiments, the drill bit protective sheath height may be chosen to specifically facilitate regulation of the depth of the drilling achieved.

In some embodiments, the drill bit protective sheath will accommodate any commercially available, standard drill-bit known in the art, which will not comprise lateral extensions and the same is still useful in any of the methods and as part of any of the kits as described herein, as will be appreciated by the skilled artisan. Such standard bit will not, when used with the drill bit protective sheath, provide for a stopper mechanism, but the skilled artisan will appreciate how to regulate the drilling depth manually.

In some embodiments, the drill bit protective sheath will be first positioned over the K-wire, with an appropriate drill bit being threaded over the K-wire and through the drill bit protective sheath, for example, when the drill bit diameter is appropriately sized so that it is appropriate for the final hole required for the implant insertion. In some embodiments, the drill bit is first threaded over the K-wire and then the drill bit protective sheath is applied thereunto.

It is to be understood that the use of the tools and kits of the invention and the methods of the invention shall not be limited by the order of use of any of the elements as described herein and/or combination of tools used, etc. and that the invention contemplates any such variation.

In some embodiments, the cannulated drill bit will prepare a hole or void in the desired target tissue having a depth, which is shorter, longer or the same as that of the final depth of the hole or void required for implant or graft insertion.

In some embodiments, this invention provides implantation alignment tool comprising:
  a substantially cylindrical hollow body;
  a substantially hollow stabilization structure terminally joined to said substantially cylindrical hollow body by a joint region, said stabilization structure comprising:
    a first region comprising a first diameter, which first diameter is smaller than a diameter of said substantially cylindrical hollow body; and
    a second region having a second diameter, which second diameter is smaller than a diameter of said substantially cylindrical hollow body and larger than said first diameter,
    wherein said second region is sized to be of a dimension to facilitate a snug fit within the borders of a site of implantation.

In one embodiment of the implantation alignment tool of this invention, at least a portion of a first region, at least a portion of a second region or a combination thereof form terminal contacts with a boundary of an implantation site.

In some embodiments, according to this aspect, the substantially cylindrical hollow body comprises a material that is a metal, metal alloy, ceramic, glass or plastic or any appropriate material described herein with respect to other tools of this invention.

In some embodiments, according to this aspect, the substantially hollow stabilization structure comprises a material as herein described and may, in some embodiments, incorporate a flexible or shock-absorbing material, such as, a silicon, sponge, a polymer, a biocompatible polymer or others as will be appreciated by the skilled artisan.

In some embodiments, an advantage to the use of the implantation alignment tool as herein described is that when it is inserted correctly, it allows the surgical cutter to be threaded thereunto and promotes stable and perpendicular positioning of the cutter even during tamping and/or prevents k-wire bending and/or permits bone collapse within the created void during cutting.

In some embodiments, the reduction of the diameter and reduction of material in the distal end of the implantation alignment tool promotes maintenance of a gap between the bone mark and the alignment tool outer surface, so that when the cutter is employed, this gap enables the bone to collapse inside the surgical cutter during tamping enhancing the ease and accuracy of the use of the cutter in carrying out the cutting procedure.

Referring now to FIGS. 4A-4B and FIG. 4E providing a higher magnification view of the alignment tool, one embodiment of an implantation alignment tool is shown. A substantially cylindrical hollow body 100 is seen, which hollow body is adapted for insertion of a rod-like structure therethrough. According to this aspect and representing an embodiment of the invention, substantially hollow stabilization structure 120 is terminally adjoined to the body section 100. The first region 110 has a first diameter, which, in some embodiments is smaller than a diameter of the body section 130 and in some embodiments is equal in diameter to that of the body section 130. The substantially hollow stabilization structure also contains a second region having a second diameter 140, which in this embodiment, is smaller than the diameter of the hollow body section 130 and in some embodiments, is larger than the first diameter 110. According to this aspect, and in some embodiments, the first region is positioned between a joint region of the substantially hollow stabilization structure attaching the same to the hollow cylindrical body and the second region.

Referring to FIGS. 4C-FIG. 4D, insertion of a rod-like structure 75 through a lumen of the implantation alignment tool is shown, with FIG. 4D providing a view of a cross section taken from the tool of FIG. 4C, at the dotted line along the midline of the tool.

FIG. 4E provides a magnified view of an embodied stabilization structure inserted within a potential graft and/or implantation site. In this aspect, the first region 110 has a diameter that is smaller than that of the hollow body section 130, yet is larger in diameter than that of the second region 140.

In some embodiments of the methods of this invention, the method comprises the steps of inserting a rod-like structure within an implantation site in a subject with the aid of an implement orienting said rod-like structure to be in an orientation perpendicular to a plane of a surface of said target implantation site; applying an implement comprising a terminally located drill bit over a rod-like structure and drilling an area of tissue in said subject which is less than that of a desired implantation site, or applying an implantation alignment tool comprising a terminal modification to approximate a drill bit, or screw-like structure, or structure approximating a structure commonly associated with a screwdriver tool, for example, a "Phillips head" type structure, or in some embodiments, any structure that facilitates creating a hole or void within the tissue to which the tool is applied.

Referring to FIGS. 4F-4I, the terminal modification 120 depicted in FIGS. 4F and 4H indeed approximate a drill bit or "Phillips head" attachment, respectively. FIGS. 4G and 4I, represent cross sections of FIGS. 4F and 4H, respectively, showing that the tool may comprise an internal lumen 105, through with a rod-like structure may be inserted.

In some embodiments, the implement may be positioned within a drill bit protective sheath, as herein described.

According to some embodiments of the implantation alignment tool of this invention, a first region is proximal to a joint region and said second region is proximal to a first region and distal to said joint region, as depicted in FIGS. 4 (A-I) and 5 (A-J). In some embodiments, a first region is proximal to a joint region and said second region is proximal to a first region and distal to said joint region, such as for example, in FIG. 5D, however, a third region 150 may have still a third diameter, which is equal to that of the diameter of the second region 140, or larger than a diameter of the second region 140. The invention also contemplates an implantation alignment tool wherein the third region has a third diameter which is smaller than the diameter of the second region 140.

According to some embodiments of the implantation alignment tool of this invention, a stabilization structure may comprise alternating first and second regions arranged in a desired pattern (FIGS. 5A-5C, and FIGS. 5E-5H). In some embodiments, according to this aspect, a second region or at least a portion thereof is located at a distal terminus of said stabilization structure, for example, as depicted in FIGS. 5A-5C, 5G and 5H.

It will be appreciated that other patterns or alternating first and second regions of the stabilization structure are possible, which structures facilitate a tight fit of the alignment tool within a defect site, which in some embodiments facilitates anchoring the tool therewithin.

In some embodiments, as noted with respect to FIG. 4, the implantation alignment tool may comprise a "Phillips head" terminal modification FIG. 5J, which may also serve as a drill bit, as described.

In some aspects, the implantation alignment tools of this invention are envisioned to approximate the structure depicted in FIG. 5I, whereby the stabilization structure contains only a single region 140 which has a diameter narrower than that of the hollow body section 130.

According to some embodiments of the implantation alignment tool of this invention, a stabilization structure may comprise a second region contains terminally extending scoring protrusions, which serve to score the walls of the defect/implantation site, to encourage blood flow within the implantation site.

In some embodiments, scoring of part of the walls, including the floor of the defect site does not preclude the preparation of a smoothed tissue implant site.

According to some embodiments of the implantation alignment tool of this invention, stabilization structure comprises alternating first and second regions resembling a screw structure, for example, as depicted in FIG. 5H. We note that according to this aspect, and representing embodied kits and methods of this invention, it is possible to forego use of a drill bit assembly as described hereinabove to create an initially drilled hole within the graft extraction and/or implantation site, and instead employ the implantation alignment tools as herein described containing the screw-like structure, which can serve to stabilize the alignment tool over the rod like structure within the defect/implantation site. A protective sleeve as herein described may be placed over the implantation alignment tool as described according to this aspect, as will be appreciated by the skilled artisan.

In some embodiments of the implantation alignment tool of this invention, a stabilization structure may comprise alternating first and second regions along a horizontal axis of said stabilization structure.

FIGS. 5G-5H depict such alternating first and second regions along a horizontal axis of said stabilization structure. In FIG. 5G, 3 alternating first and second regions are depicted at intervals along a horizontal axis of the implantation alignment tool. Such intervals may be equi-spaced, or the spacing may be non-equidistant, as will be appreciated by the skilled artisan.

FIG. 5H depicts a helical overall arrangement of alternating first and second regions. It will be appreciated by the skilled artisan that the pitch of such helical structure, for example including the width of the first and second regions, and/or the angle of rotation of each may vary, and such variability is contemplated by the invention.

In some embodiments of the implantation alignment tool of this invention, a stabilization structure may comprise alternating first and second regions along a vertical axis of said stabilization structure. Embodied aspects of such arrangements are depicted in FIGS. 5A, 5B, 5C, 5E and 5F.

In FIGS. 5A, 5B and 5C, a similar overall orientation of the first and second region is shown, where the regions substantially alternate along a vertical axis, wherein the most terminal region of the tool, which is most proximally placed to the implantation or graft site is the second region 110, and the alternating placement of the first region 140 does not promote terminal placement, which is most proximally placed to the implantation or graft site of the first region.

FIGS. 5E and 5F depict embodiments, whereby both first and second regions contain at least a portion thereof, which may be in contact with the implantation or graft site.

It will be appreciated that there are a number of configurations of the first and second region, which will facilitate a tight fit within the created void, thereby promoting appropriate alignment of the tool within the void, to promote effective application of the surgical cutter, to enlarge a void first formed, as herein described.

As the implantation tool alignment implement fits over the rod-like structure, which has been implanted within a target tissue site, it contains a hollow substantially cylindrical body 100, which may have a diameter such that a tight fit is formed between an outer surface of the rod-like structure and an inner surface of the hollow body. In other embodiments, the diameter of the hollow body may be larger than that of the rod-like structure, such that the insertion of the rod-like structure therewithin is stabilized by the presence of at least one adapter 155 within the lumen of the hollow body section. The adapter may possess all of the embodied aspects described for the adapter in connection with the implantation tool stabilizing implement described hereinabove.

In some embodiments, the implantation tool alignment implement insertion over the rod-like structure allows for incorporation of a terminus of the implement within the drilled target tissue site in a press fit manner. In some embodiments, such structure and organization provides for an orientation of the implement to be perpendicular to a target tissue surface.

In some embodiments, the implantation tool alignment implement contains a terminal modification to include a reduction of the diameter 110, 140, 150 as compared to the body section diameter located proximally thereto 130.

In one aspect, the distal modification creates a step-like structure in the alignment implement, which may be understood to serve as a stabilizing mechanism, preventing unlimited advancement of the alignment implement within the drilled area of the target tissue site.

In some embodiments, the distal modification creating a step-like structure in the alignment implement can be readily prepared by standard means in the art, as will be appreciated by the skilled artisan, for example, by removing material from the perimeter of a terminus of the alignment implement, by machining, etc.

In some embodiments, the alignment implement may be comprised of any appropriate material. Non-limiting examples of the same may include any biocompatible material, such as a metal, plastic or glass, comprised of a polymer, ceramic, etc.

In some embodiments, the invention includes a kit comprising an implantation tool alignment implement as herein described, alone or in combination with any of the tools and/or parts as herein described, including solid implants of any desired size or size range, as will be appreciated by the skilled artisan.

In some embodiments, this invention provides a tissue harvester assembly, comprising:
an implantation tool alignment implement as herein described; and
a surgical cutter;
wherein the surgical cutter is adapted to fit over said implantation alignment tool in situ and the alignment tool maintains a desired orientation of the surgical cutter during tissue harvest with the aid of said tissue harvester assembly.

According to this aspect, and in some embodiments, the surgical cutter is so constructed so as to comprise a substantially cylindrical hollow body, which in turn may provide for insertion of the implantation tool alignment implement therewithin.

In some embodiments, the surgical cutter may also contain identification marks that provide a guide as to the insertion depth of the cutter, for example, by incorporating laser marks on the outer surface of the cutter region inserting within the target tissue.

In some embodiments, the fact that the implantation tool alignment implement possesses a terminal modification to contain a reduction in diameter 140, which is also narrower than the drilled region, provides for the presence of a gap between the bone, for example, subchondral bone and alignment implement. In some embodiments, the presence of such a gap enables the tide mark to collapse inside the surgical cutter while the same is being tamped down as part of the procedure to enlarge the drill site thereby facilitating greater penetration of the cutter and in some embodiments, greater ease and accuracy of insertion and enlargement of the drilled tissue site.

In some embodiments, turning to FIGS. 6 (A-D)-7 (A-G), showing some embodied surgical cutters for use with the other tools and kits as herein described and as part of the methods of this invention, embodied surgical cutters are shown. In one aspect a tamping head 160 is shown within a handle 165, connected to a shaft 170 of the cutter tool. The cutter tool may optionally comprise a security nut locker 175 between the surgical cutter tip 180 and handle 165, and a blade cutter tip, for example, a round blade cutter metal tip 180. The surgical cutter will be cannulated, i.e. it will contain an inner channel through which an alignment tool and/or rod-like structure may insert 185. The surgical cutter may be a modular tool, in some embodiments, and thus certain elements of the cutter tool may be detachable, as will be appreciated by the skilled artisan. In some embodiments, the handle and upper tool region is detachably connected to a blade cutter tip region, attachable at, for example, a connection point 220 between the round blade cutter tip and the round blade cutter handle. In some embodiments, the blade is interchangeable, for example, and blade tips 200 are exchangeable.

FIGS. 6 (A-D)-7(A-G) provide an exploded view of exemplified surgical cutters/reamers/smoothers of this invention, and in some embodiments, as part of a kit or for use in a method of this invention, which exploded view facilitates ease of view of the individual parts of the tool. In some embodiments, the exploded view also provides an understanding as to how the cutter/reamer/smoother may be a modular tool, enabling rejoining of some of the parts of the tool with alternate embodied elements, for example, the depicted handle with another cutter tip or vice versa.

In some embodiments, the surgical cutter/reamer/smoother comprises a removable blade cutter head 180/smoothing head 300/reamer head 310 is adapted for connection via 200, which is removably attachable to a handle part 230. In some embodiments, the removable blade cutter head 180/smoothing head 300/reamer head 310 may comprise adaptations for effective joining with an appropriately modified handle part, for example, a "nut"-like locker 175, and for example, a "teeth"-like structure in the removable blade cutter head 210 may fit and thereby join a corresponding grooved section on the handle part 220. In some embodiments, the surgical cutter/smoother/reamer may comprise demarcations 195, which provide a means for depth measurement of the advancement of the tool within the tissue void.

The term "surgical cutter" as used herein may refer to a tool that creates a void in a tissue, or in some embodiments removes a desired amount of tissue, or in some embodiments, enlarges a void in a tissue, or in some embodiments, shapes a void in a tissue.

In some embodiments, the prepared void may be enlarged laterally or in terms of its depth, via the use of a reamer as herein described. According to some aspects, the reamer may have a comparable structure to the surgical cutter, including demarcations identifying a depth achieved when employed in situ.

In some embodiments, the prepared void may be smoothed in terms of the relative uniformity of the boundary surface via the use of a smoother as herein described.

In some embodiments, the choice of term with respect to "surgical cutter" or "reamer" or "smoothing tool", may depend upon whether the indicated tools is used only for creating a void/removing tissue or enlarging/shaping a void, respectively. It will be appreciated that a single tool with interchangeable heads may be used to accommodate the three functions of cutting, reaming and smoothing a void, and the term "surgical cutter" and any embodiment as described with respect thereto, may be understood to encompass a tool that may create/enlarge/smooth a void, as well.

Referring to FIG. 6B, an exemplified smoothing tool is shown, which smoother is also to be construed as being a type of surgical cutter tool. The smoothing tool may comprise, in some embodiments, a tamping head 160, within a handle part 165. The smoothing tool extension 180 is positioned distally to the handle part 165. In some embodiments, the smoothing tool may further comprise a scale bar and measuring aspect 195, which allows for measurement of the shaped region created for implantation, as herein described. In some embodiments, the unique tools of this invention, for example via the unique handles, facilitate tissue removal without "wobbling", to ensure the boundaries of the void created are not expanded laterally.

Once the target site has been appropriately prepared to contain a void of a size and shape to be filled with one or more grafts or implants, implantation of the same may be commenced.

In some embodiments, the cutter, reamer and smoother may comprise markings, which facilitate measurement of the void created/smoothed with the same. In some embodiments, another measurement tool may be thus utilized for the measurement of the void into which the implant or graft will be fit/inserted. FIGS. 7F and 7G show a handle, which may further serve to grip, insert, or extract the k-wire or k-wire adapter. The handle may be cannulated, as evident in FIG. 7G.

In some embodiments, the invention provides an implantation scoring tool comprising:

a longitudinal body which is optionally hollow and adapted for insertion of a rod-like structure therethrough; and at least one laterally extending protrusion, which protrusion is oriented substantially perpendicularly to a long-axis of said longitudinal body, optionally wherein said laterally extending protrusion possesses a deployed and a compact position;

wherein when said implantation scoring tool is placed within an implant site and said laterally extending protrusion is in its deployed position, said laterally extending protrusion inserts within a tissue wall bounding said implant site thereby scoring said tissue wall.

In some embodiments, the invention provides kits and/or methods making use of the implantation scoring tools as herein described.

Referring to FIG. 8 (A-D), as can be seen in the higher magnification views of panels 8B and 8D, the scoring tool may exist in a compact and deployed position, facilitating easy insertion within the defect/implantation site. The scoring tool when deployed facilitates increased penetrance of proximally located blood into the site promoting better implant/graft incorporation therewithin.

In some aspects the scoring tool will comprise at least an elongated body and at least one laterally extending protrusion therefrom, and in some embodiments, the scoring tool may optionally comprise a hollow along the elongated body through which a rod-like structure as herein described may insert therethrough.

In some embodiments, this invention provides a graft or solid implant introducing tool suitable for the introduction of brittle grafts or solid implants, said graft or solid implant introducing tool comprising:

a piston assembly containing a substantially elongated body and a first terminus comprised of a shock-absorbant material and an advancer structure located at a second terminus of said substantially elongated body; and a substantially hollow substantially cylindrical body into which a piston assembly may insert flanked by an open insertion region and a graft or solid implant containment gripping part and further comprising a stopper region positioned proximally to said implant containment gripping part, wherein said piston assembly when inserted within said cylindrical body is prevented from advancing further along a longitudinal axis of said cylindrical body when in contact with said stopper region; and said graft or solid implant containment gripping part comprises a flexible shock-absorbing material and which gripping part is sized to accommodate insertion of only a portion or full graft or solid implant therewithin.

Referring now to FIG. 9 (A-H), an embodiment of a graft or solid implant introducing tool is shown in assembled and exploded view. The introducing tool or introducer comprises a piston assembly 245 containing a first terminus comprised of a shock-absorbant material 270 and an advancer or "tamper" structure located at a second terminus 245. The piston assembly of the introducer inserts within a substantially hollow substantially cylindrical body 255 which comprises a graft or solid implant containment gripping part 265 which holds the graft or solid implant 275. In some embodiments, such arrangement allows, inter alia, for controlled insertion of the implant, with concordant protection of the boundaries of the implant site.

Figure 9H:
FIG. 9 (A-H) schematically depict embodiments of graft or solid implant, introducing tools of this invention and for use in the methods of this invention, including graft or solid implant introducing tools comprising a hollowed region through which a rod-like structure, such as a K-wire may insert.
Figure 9G:
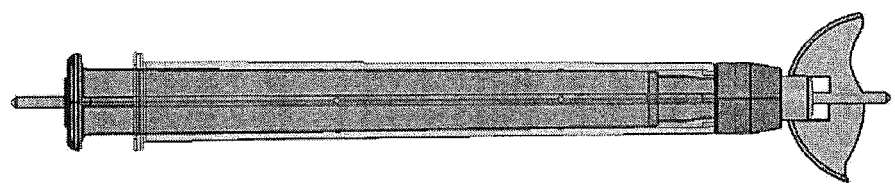
Figures 9E, 9F:
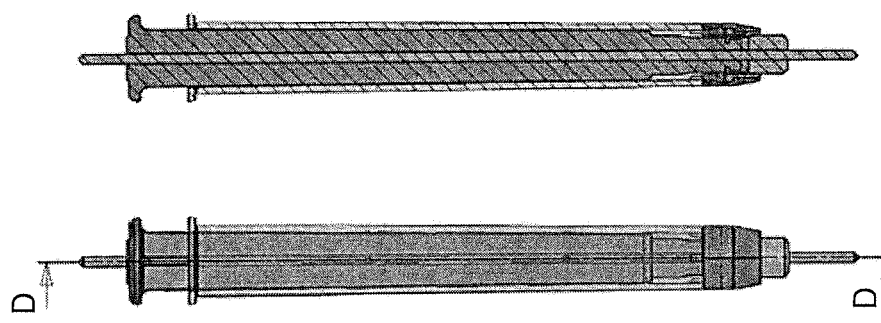
Figure 9D:
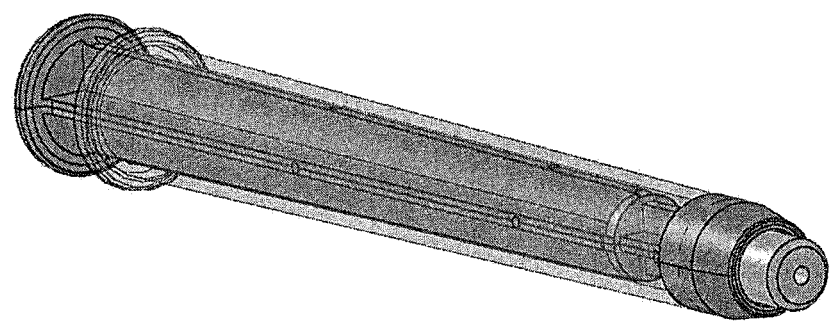
Figure 10F:
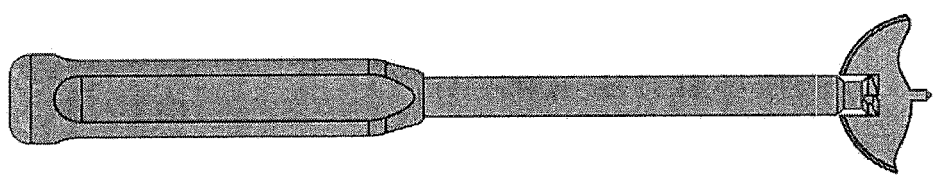
FIG. 10 (A-I) schematically depict embodiments of an embodied implantation tool stabilizing implement, including insertion of a rod-like structure therethrough, a drill bit assembly unit, implantation alignment tool, surgical cutter, reamer and smoothing tool of this invention and for use in accordance with the methods of this invention. Kits of this invention envisioned include the full complement of tools described in FIG. 10, or one or more tool combinations of the tools of this invention.
Figure 10E:
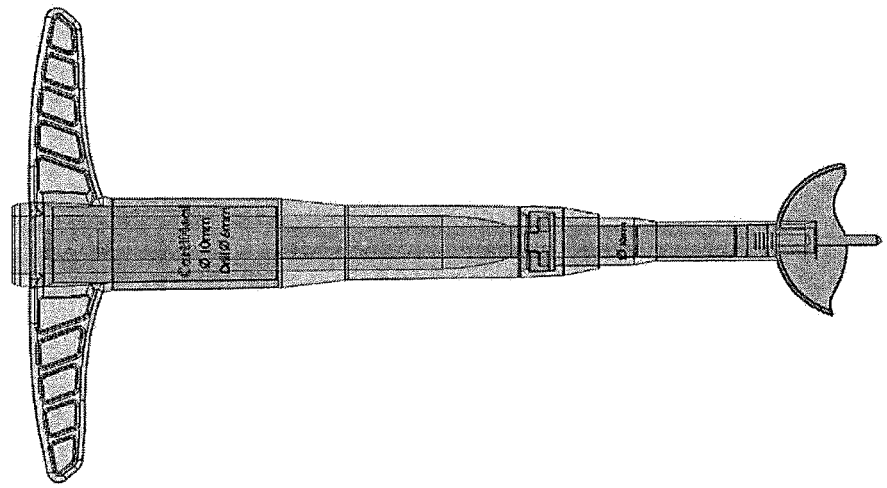
Figure 10D:
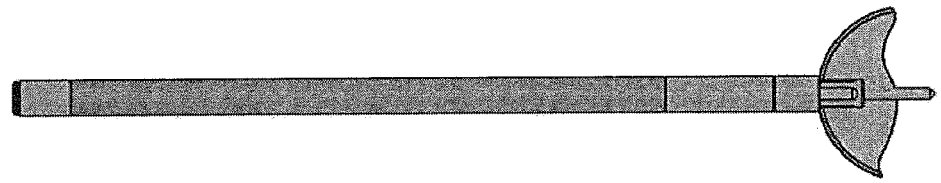
Figure 10C:
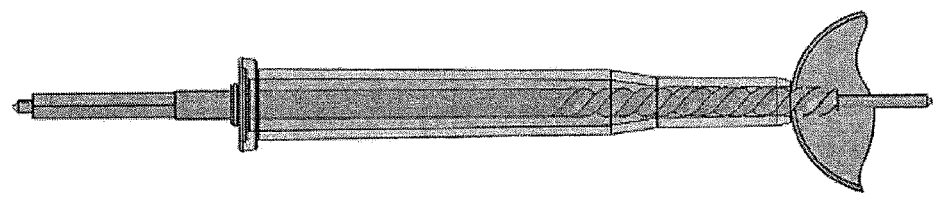
Figures 10A, 10B:
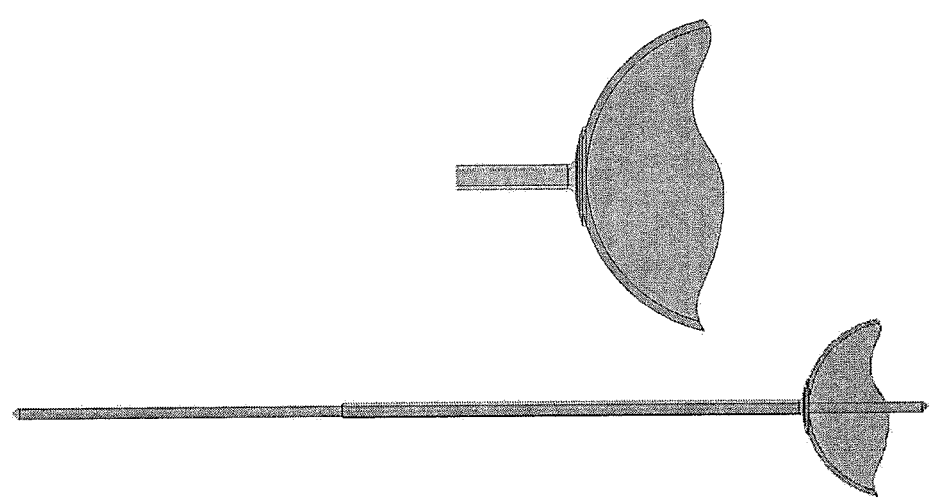
Figure 10I:
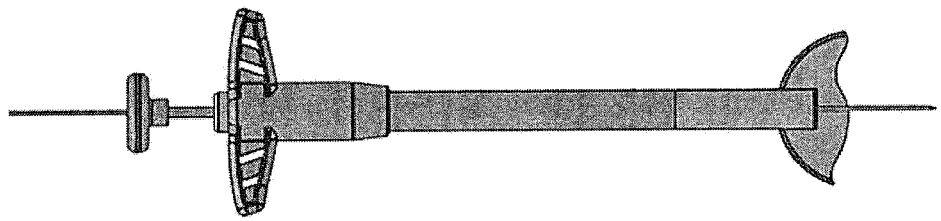
Figure 10H:
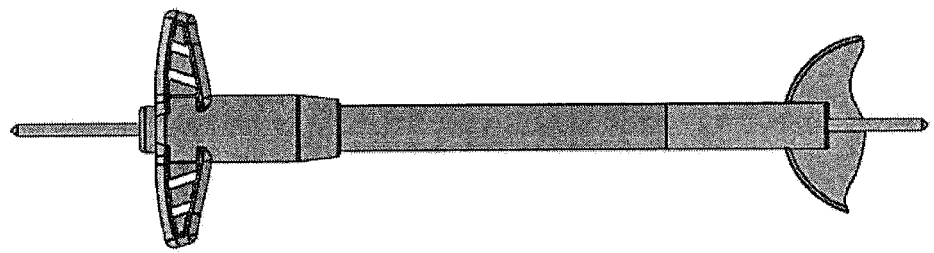
Figure 10G:
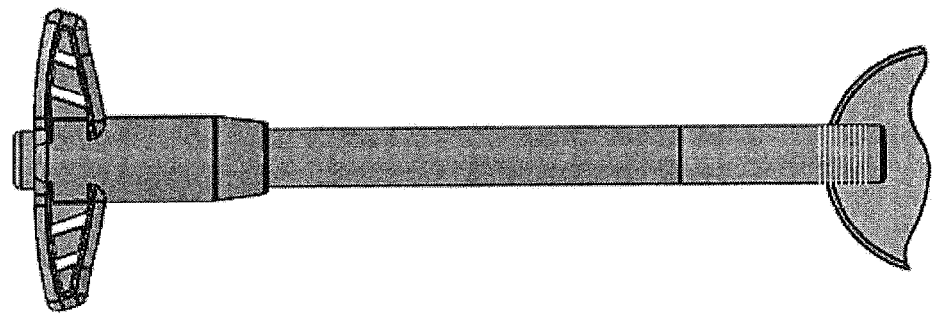
Figure 11A:
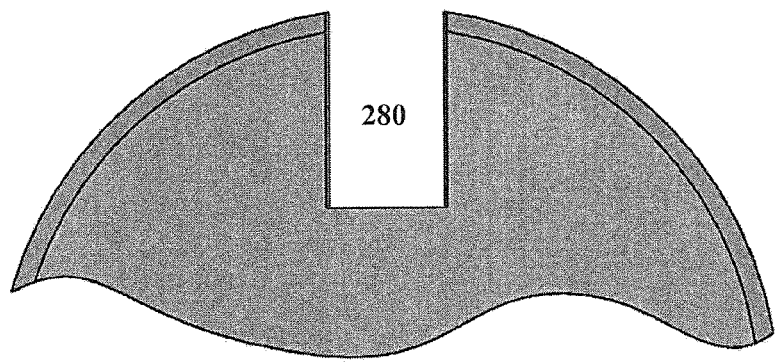
FIG. 11 (A-C) schematically depict a more magnified view of the creation of an appropriate implantation or graft site, insertion of a graft or solid implant introducing tool containing the desired graft or solid implant therewithin and an embodied implantation of a desired implant or graft being accomplished in a tight-fit.
Figure 11B:
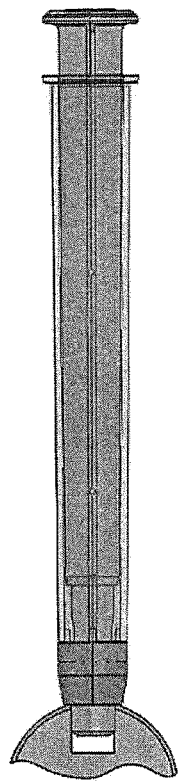
Figure 11C:
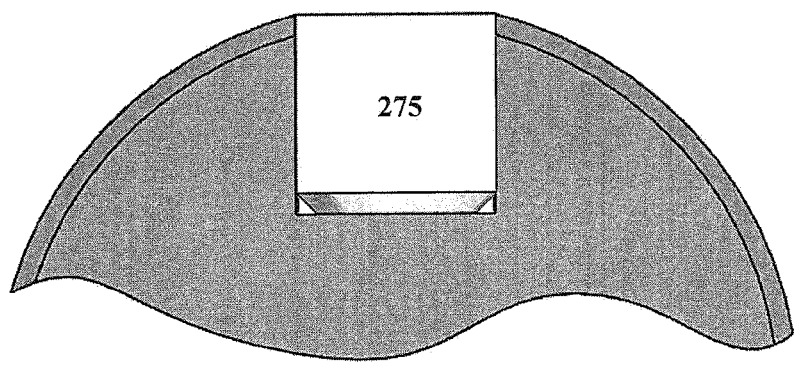

In some embodiments, the graft or solid implant introducing tool comprises a hollow along a longitudinal axis throughout the elements of the tool, facilitating placement of the tool over a rod-like structure. In some embodiments, the graft or implant may comprise a hollow along a longitudinal axis therein, as well for ease of placement thereupon. In some embodiments, the tamper element contains a hollow along a longitudinal axis throughout the tamper, as well (FIG. 9H).

In some embodiments, the graft or solid implant introducing tool comprises a combined assembly, whereby the tamper can advance the implant, optionally comprising a terminally located gripper, and a modified head at the second terminus, such that the tamper and implant are cannulated and can be placed over the rod like structure within the void, and force may be applied to the tamper terminus for optimum fit of the implant within the implantation site.

Without being bound by theory, in some embodiments, the introducing tool facilitates proper orientation of the implant within the site; in some embodiments the tool is helpful in maintaining safe placement of the implant during arthroscopy procedures/implantation procedures.

In some embodiments, this invention provides a graft or solid implant introducing tool suitable for the introduction of brittle grafts or solid implants, said graft or solid implant introducing tool comprising:
  a piston assembly containing a substantially elongated body, which optionally contains a hollow through which a rod-like structure may insert and a first terminus comprised of a shock-absorbant material and an advancer structure located at a second terminus of said substantially elongated body; and
  a sheath which sheath accommodates insertion of said piston assembly therewithin, which sheath comprises:
  an insertion region for insertion of said piston assembly;
  a substantially hollow substantially cylindrical body into which said piston assembly may insert;
  optionally a stopper region located proximally to said piston assembly when said piston assembly is inserted within said substantially hollow substantially cylindrical body, wherein said stopper region comprises a solid boundary containing an opening, which opening accommodates insertion of only a portion of said first terminus of said piston assembly;
  optionally a stopper indicator region located proximally to said a graft or solid implant containment part, which indicator region may comprise a mark identifying optimal advancement of the graft or solid implant; and
  a graft or solid implant containment part located proximally to said solid boundary of said stopper region, which part is comprised of a flexible shock-absorbing material and which part is optionally sized to accommodate insertion of only a portion of a graft or solid implant therewithin or which part will abut placement of said graft or solid implant placed proximally thereto.

In some embodiments, the stopper indicator region may include identifying marks on both the graft or solid implant containment part and on the sheath, and their alignment or combined configuration identifies optimal placement of said graft or implant. In other embodiments, the sheath may comprise a "window" or visible region such that when said the graft or solid implant containment part and achieves a desired advancement therewithin, visualization of the containment part within the window, or visualization of a symbol within such window serves as the identifying mark.

In some embodiments, this invention provides a graft or solid implant introducing tool suitable for the introduction of brittle grafts or solid implants, said graft or solid implant introducing tool comprising:
  a substantially elongated body, which optionally contains a hollow extending therethrough, sized to accommodate insertion of a rod-like structure;
  a first terminus comprised of a shock-absorbant material; and
  an advancer structure located at a second terminus of said substantially elongated body; and
  optionally a gripping part comprised of a flexible shock-absorbing material and which gripping part is sized to accommodate insertion of only a portion of a graft or solid implant therewithin; and/or
  optionally a rod-like structure extending through said hollow in said substantially elongated body.

According to this aspect, and representing certain embodiments of this invention, a graft or implant is placed within a gripping part of a piston assembly, or, in some embodiments, within a gripping part of the graft or solid implant introducing tool, and the tool advances the implant or graft within an implantation site.

According to this aspect, and representing certain embodiments of this invention, a graft or implant is cannulated, or in some embodiments, comprises a void along a longitudinal axis spanning a length of such graft or implant, which graft or implant may then be threaded onto a rod-like structure. In some aspects, such rod-like structure is itself threaded through the solid implant introducing tools of this invention, and the graft or implant abuts the first terminus or is contained within a gripping part of located at the first terminus of the solid implant introducing tool.

In some aspects, such rod-like structure is itself threaded through the solid implant introducing tools of this invention, and the graft or implant abuts the first terminus or is contained within a gripping part of located at the first terminus of the solid implant introducing tool. According to one aspect of this embodiment, such rod-like structure is implanted within a tissue containing a prospective implantation site, and said graft or implant and the solid implant introducing tool are both threaded onto the rod-like structure in situ, whereby the advancing part of the solid implant introducing tool is used to advance the graft or implant to create an appropriate fit of the graft or implant within the implant site.

As noted hereinabove, the invention provides a highly stable means of introducing solid implants and/or grafts, in particular in introducing the same within solid tissue. FIGS. 10 (A-I) and 11(A-C) provide a general description of contemplated embodiments of the tools of this invention/means for use in accordance with the methods of this invention, including a close up view of placement and/or insertion of the same with respect to a surface of or within a target tissue.

Figure 12C:
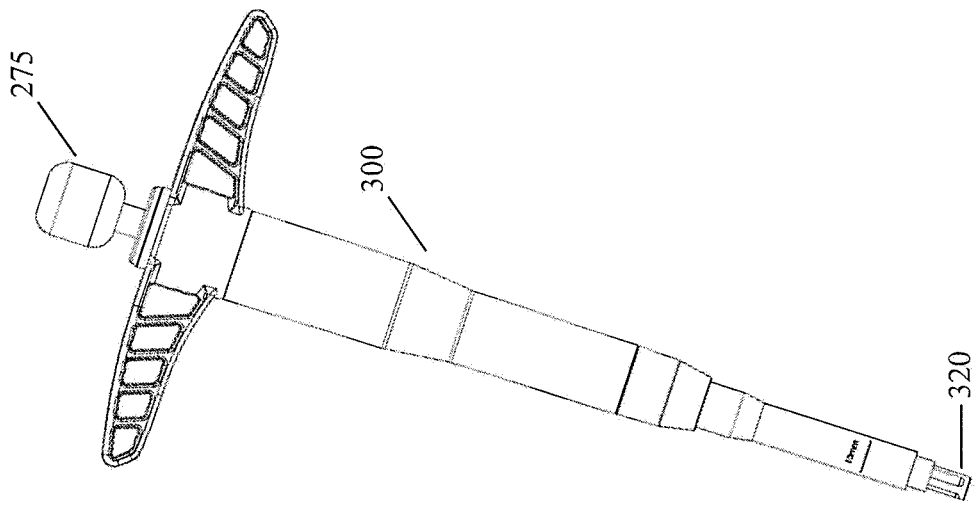
FIG. 12 (A-C) schematically depict a view of an embodied extractor tool, which in some embodiments, removes the implantation tool stabilizing implement upon application of the surgical cutter thereon.
Figure 12B:
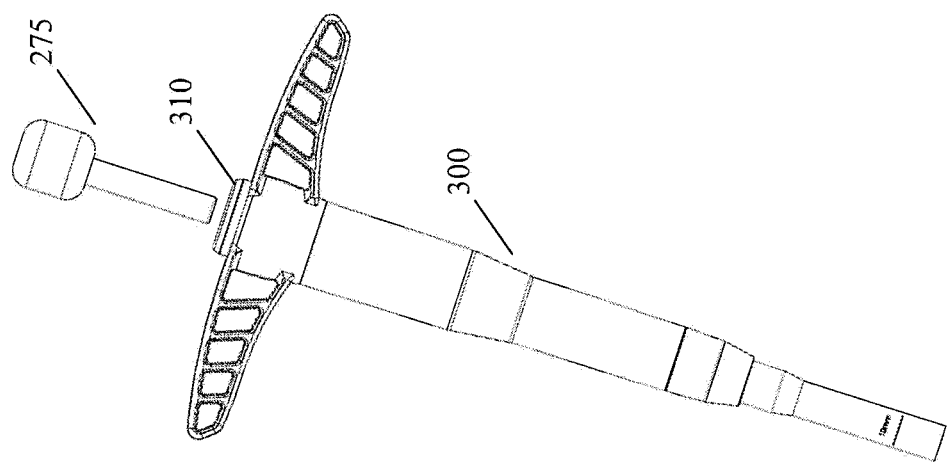
Figure 12A:
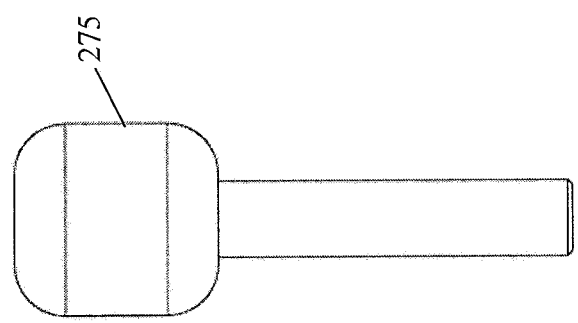

FIG. 12 (A-C) schematically depicts an embodied extractor tool 275, which in some embodiments, removes the implantation alignment tool upon application of the surgical cutter thereon. In some aspects, the extractor tool 275 fits within an apical void 310 in the surgical cutter 300 and attaches onto an implantation alignment tool 320 located beneath the cutter.

FIG. 13 (A-H) schematically depicts certain steps in an embodied implantation procedure using embodied tools of this invention, whereby a thicker rod like-structure is replaced with a thinner rod-like structure following preparation of the implantation site, for eventual threading and implantation of a graft or implant within such site. According to this aspect, and in some embodiments, the ultimate graft/implant for insertion will be cannulated, having a diameter that may be narrower than that of a first rod-like structure inserted within an implantation site.

Referring now to FIG. 13A, according to this aspect, in one embodiment, following application of the surgical cutter, reamer, smoother, shaper, etc., (any of which is represented by 340) which may be applied over the implantation alignment tools of this invention, removal of the implantation alignment tool may be accomplished, for example, via use of the extractor tool, following which the first rod-like structure 330 is removed from the implantation site (FIG. 13B) and a second thinner rod-like structure is inserted. In some embodiments, the implantation alignment tool is not removed, and only the first rod-like structure 330 is removed from the implantation site and a second thinner rod-like structure is inserted.

In some embodiments, the smoother/reamer/cutter/shaper will contain an adapter 350, which inserts within the lumen of the smoother/reamer/cutter/shaper. In some aspects, the adapter may extend vertically for a substantial length within the lumen of the smoother/reamer/cutter/shaper (FIG. 13C). A second thinner rod-like structure 360 may then be inserted (FIG. 13D).

Figure 13H:
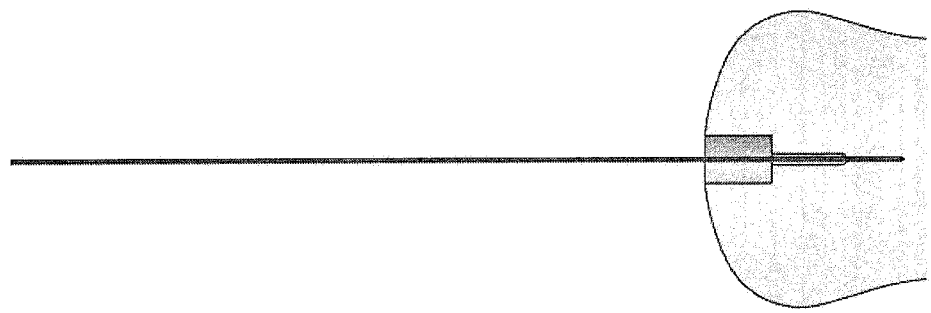
FIG. 13 (A-H) schematically depict certain steps in an embodied implantation procedure using embodied tools of this invention, whereby a thicker rod like-structure is replaced with a thinner rod-like structure following preparation of the implantation site, for eventual threading and implantation of a graft or implant within such site.
Figure 13G:
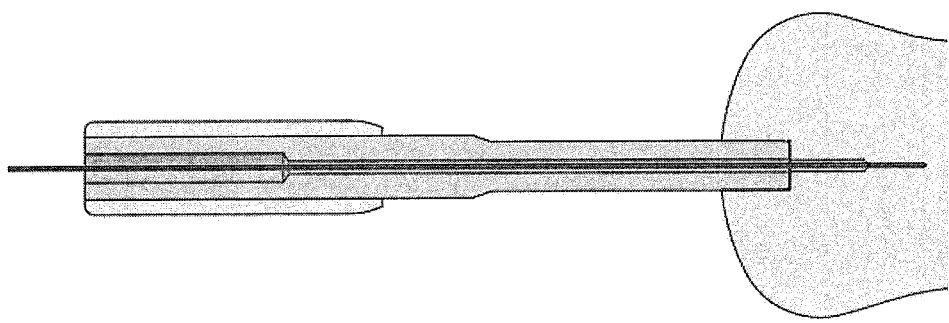
Figure 13F:
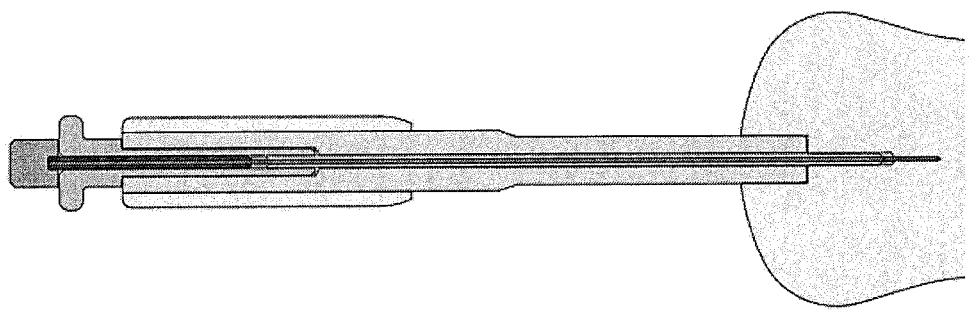

In some aspects, an apical protective cap 370 may be applied to the second thinner rod like structure 360 (FIG. 13E). Such a cap may be sufficiently strong so that application of force to the same advances the second thinner rod-like structure 360 deeper into the underlying tissue (FIG. 13F). In some aspects, the cap may be fitted with extensions, which insert into the lumen of the smoother/reamer/cutter/shaper such then when force is applied, the second thinner rod like structure 360 is not bent. The protective cap and adaptor may then be removed (FIG. 13G) and smoother/reamer/cutter/shaper are removed, as well (FIG. 13H), following application of the implant The second rod-like structure may then be removed, leaving the graft/implant within the desired implantation site, in tight fitted, optimally placed manner.

Figure 15:
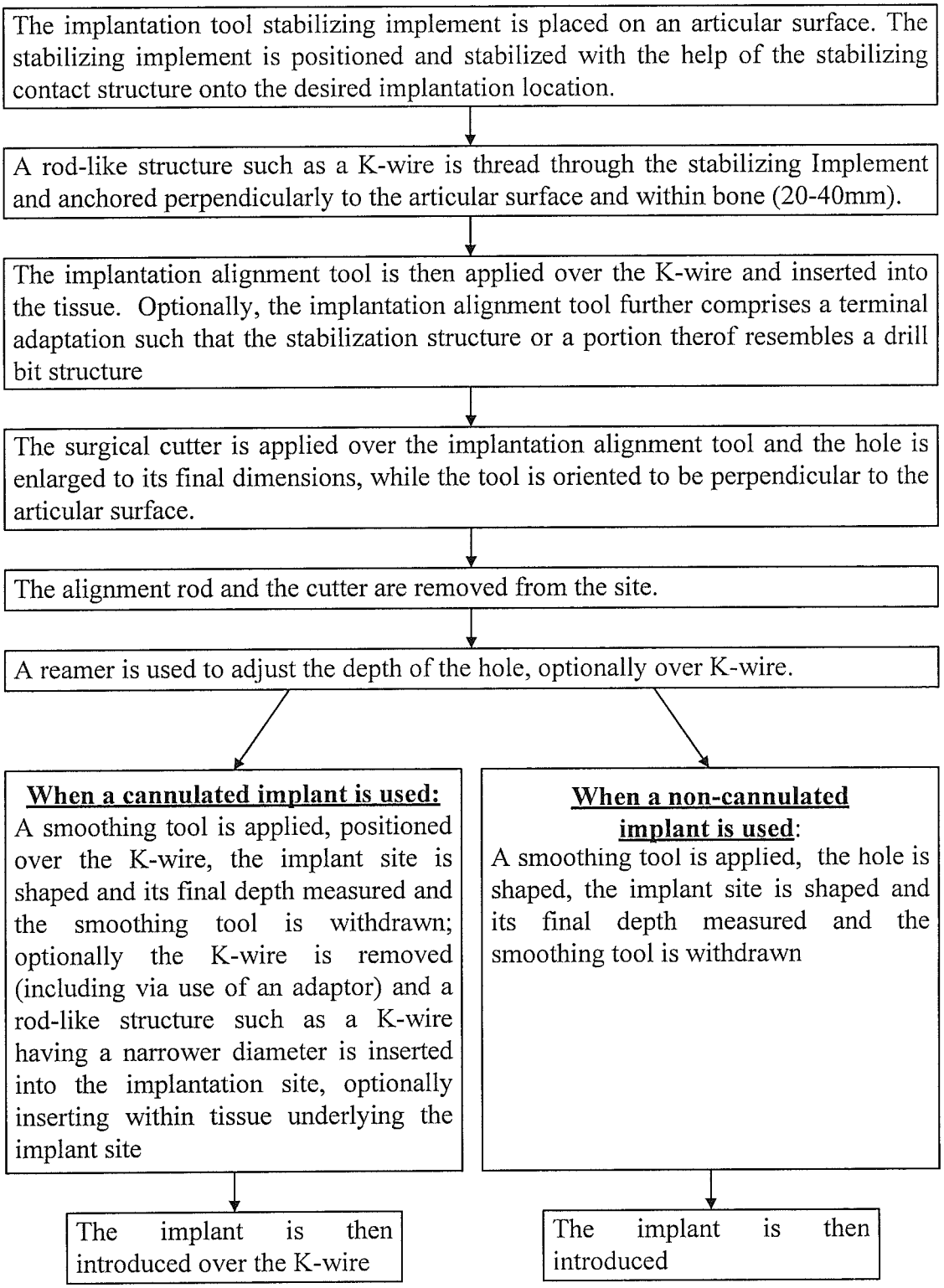
FIG. 15 provides a second flow chart illustrating another embodied procedure for introducing a graft or solid implant into a subject, making use of the tools of this invention.

FIGS. 14 and 15 provides flow charts illustrating embodied procedures for introducing a graft or solid implant into a subject, making use of the tools of this invention.

It is to be understood that the tools and methods and kits as herein described may be used to implant one or more grafts or implants and the same may be accomplished via obvious modifications, for example, creation of multiple voids, or shaping of a larger void in order to accommodate multiple grafts or implants, and that the same may provide for an ability to repair larger osteochondral or bone defects, as the skilled artisan will appreciate.

It will be understood by those skilled in the art that various changes in form and details may be made therein without departing from the spirit and scope of the invention as set forth in the appended claims. Those skilled in the art will recognize, or be able to ascertain using no more than routine experimentation, many equivalents to the specific embodiments of the invention described herein. Such equivalents are intended to be encompassed in the scope of the claims.

Articles such as "a,", "an" and "the" mean one or more than one unless indicated to the contrary or otherwise evident from the context. Claims or descriptions that include "or" or "and/or" between members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention provides, in various embodiments, all variations, combinations, and permutations in which one or more limitations, elements, clauses, descriptive terms, etc., from one or more of the listed claims is introduced into another claim dependent on the same base claim unless otherwise indicated or unless it would be evident to one of ordinary skill in the art that a contradiction or inconsistency would arise. Where elements are presented as lists, e.g. in Markush group format or the like, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in haec verba herein. Certain claims are presented in dependent form for the sake of convenience, but Applicant reserves the right to rewrite any dependent claim in independent format to include the elements or limitations of the independent claim and any other claim(s) on which such claim depends, and such rewritten claim is to be considered equivalent in all respects to the dependent claim in whatever form it is in (either amended or unamended) prior to being rewritten in independent format.

The invention claimed is:

1. An implantation tool stabilizing implement comprising:
    a hollow elongated body adapted for insertion of a rod-like structure therethrough; and
    at least one stabilizing contact structure comprising an at least partially circular concave structure having an inner tissue contact surface and an outer visualization surface, and an aperture adapted for insertion of said rod-like structure therethrough, located centrally within said structure and spanning said structure,
    further comprising an adapter, which adapter possesses a diameter that is smaller than that of said hollow elongated body and which diameter is larger than said rod-like structure's diameter, wherein said adapter is placed within said hollow elongated body and said rod-like structure may be inserted therethrough.

2. The implantation tool stabilizing implement of claim 1, wherein said hollow elongated body is a hollow cylindrical body that is sized to accommodate insertion of a K-wire therethrough.

3. The implantation tool stabilizing implement of claim 1, wherein said hollow elongated body is a hollow cylindrical body and said hollow cylindrical body's diameter is, in comparison to said rod-like structure's diameter, such that insertion of said rod-like structure therethrough leaves a space between said rod-like structure's outer surface and said hollow cylindrical body's internal surface.

4. The implantation tool stabilizing implement of claim 1, wherein said at least partially circular concave structure is comprised of a transparent or translucent material.

5. The implantation tool stabilizing implement of claim 1, wherein said hollow elongated body and said at least one stabilizing contact structure are comprised of a metal, metal alloy, glass or plastic.

6. The implantation tool stabilizing implement of claim 5, wherein said hollow elongated body is a hollow cylindrical body, wherein said hollow cylindrical body and said at least one stabilizing contact region are comprised of a different material.

7. The implantation tool stabilizing implement of claim 6, wherein said hollow cylindrical body is comprised of a metal or metal alloy.

8. The implantation tool stabilizing implement of claim 6, wherein said hollow cylindrical body is comprised of a plastic or glass.

9. The implantation tool stabilizing implement of claim 5, wherein said hollow elongated body is a hollow cylindrical body, wherein said hollow cylindrical body and said at least one stabilizing contact structure are comprised of the same material.

10. The implantation tool stabilizing implement of claim 1, wherein said hollow elongated body is a hollow cylindrical body, and wherein said hollow cylindrical body and said at least one stabilizing contact structure are comprised of the same material.

11. An implantation tool stabilizing implement comprising:
   a hollow elongated body adapted for insertion of a rod-like structure therethrough; and
   at least one stabilizing contact structure comprising an at least partially circular concave structure having an inner tissue contact surface and an outer visualization surface, and an aperture adapted for insertion of said rod-like structure therethrough, located centrally within said structure and spanning said structure;
   wherein said at least partially circular concave structure is comprised of a transparent or translucent material.

12. The implantation tool stabilizing implement of claim 11, wherein said hollow elongated body is a hollow cylindrical body that is sized to accommodate insertion of a K-wire therethrough.

13. The implantation tool stabilizing implement of claim 11, wherein said hollow elongated body is a hollow cylindrical body and said hollow cylindrical body's diameter is, in comparison to said rod-like structure's diameter, such that insertion of said rod-like structure therethrough leaves a space between said rod-like structure's outer surface and said hollow cylindrical body's internal surface.

14. The implantation tool stabilizing implement of claim 11, wherein said hollow elongated body and said at least one stabilizing contact structure are comprised of a metal, metal alloy, glass or plastic.

15. The implantation tool stabilizing implement of claim 14, wherein said hollow elongated body is a hollow cylindrical body, wherein said hollow cylindrical body and said at least one stabilizing contact region are comprised of a different material.

16. The implantation tool stabilizing implement of claim 15, wherein said hollow cylindrical body is comprised of a metal or metal alloy.

17. The implantation tool stabilizing implement of claim 15, wherein said hollow cylindrical body is comprised of a plastic or glass.

18. The implantation tool stabilizing implement of claim 14, wherein said hollow elongated body is a hollow cylindrical body, wherein said hollow cylindrical body and said at least one stabilizing contact structure are comprised of the same material.

19. The implantation tool stabilizing implement of claim 11, wherein said hollow elongated body is a hollow cylindrical body, and wherein said hollow cylindrical body and said at least one stabilizing contact structure are comprised of the same material.

* * * * *